(12) United States Patent
Morrissette et al.

(10) Patent No.: US 8,939,894 B2
(45) Date of Patent: Jan. 27, 2015

(54) THREE-DIMENSIONAL TARGET DEVICES, ASSEMBLIES AND METHODS FOR CALIBRATING AN ENDOSCOPIC CAMERA

(71) Applicants: Tyler J. Morrissette, Niantic, CT (US); Tao Zhao, Sunnyvale, CA (US); Joseph P. Orban, III, Norwalk, CT (US); Brian David Hoffman, Mountain View, CA (US)

(72) Inventors: Tyler J. Morrissette, Niantic, CT (US); Tao Zhao, Sunnyvale, CA (US); Joseph P. Orban, III, Norwalk, CT (US); Brian David Hoffman, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/623,307

(22) Filed: Sep. 20, 2012

(65) Prior Publication Data
US 2013/0085329 A1 Apr. 4, 2013

Related U.S. Application Data

(60) Provisional application No. 61/541,427, filed on Sep. 30, 2011.

(51) Int. Cl.
*A61B 1/04* (2006.01)
*A61B 1/00* (2006.01)

(52) U.S. Cl.
CPC ......... *A61B 1/00057* (2013.01); *A61B 1/00193* (2013.01)
USPC ........................................... 600/111; 600/127

(58) Field of Classification Search
USPC ............... 348/45; 702/94; 600/111, 127, 129; 356/241.1
See application file for complete search history.

(56) References Cited

U.S. PATENT DOCUMENTS

| | | | | |
|---|---|---|---|---|
| 5,953,112 A | * | 9/1999 | Rosow et al. | 356/73.1 |
| 7,221,733 B1 | * | 5/2007 | Takai et al. | 378/65 |
| 2005/0107808 A1 | * | 5/2005 | Evans et al. | 606/139 |
| 2007/0265497 A1 | * | 11/2007 | Brown et al. | 600/114 |
| 2008/0291278 A1 | * | 11/2008 | Zhang et al. | 348/159 |
| 2010/0168562 A1 | | 7/2010 | Zhao et al. | |

OTHER PUBLICATIONS

Tsai, Roger Y., "A Versatile Camera Calibration Technique for High-Accuracy 3D Machine Vision Metrology Using Off-the-Shelf TV Cameras and Lenses," IEEE Journal of Robotics and Automation, 1987, pp. 323-344, vol. RA-3—Issue 4, IEEE.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Anhtuan T Nguyen
*Assistant Examiner* — Timothy J Neal

(57) ABSTRACT

The present disclosure relates to calibration target devices, assemblies and methods for use with imaging systems, such as a stereoscopic endoscope. A calibration assembly includes: a target surface extends in three dimensions with calibration markers and a body with an interface that engages an endoscope so the markers are within the field of view. A first calibration marker extends along a first plane of the target surface and a second marker extends along a second plane of the target surface. The planes are different and asymmetric relative to the field of view as seen through the endoscope. Three-dimensional targets, in particular, enable endoscopic calibration using a single image (or pair of images for a stereoscopic endoscope) to reduce the calibration process complexity, calibration time and chance of error as well as allow the efficient calibration of cameras at different focus positions.

30 Claims, 18 Drawing Sheets

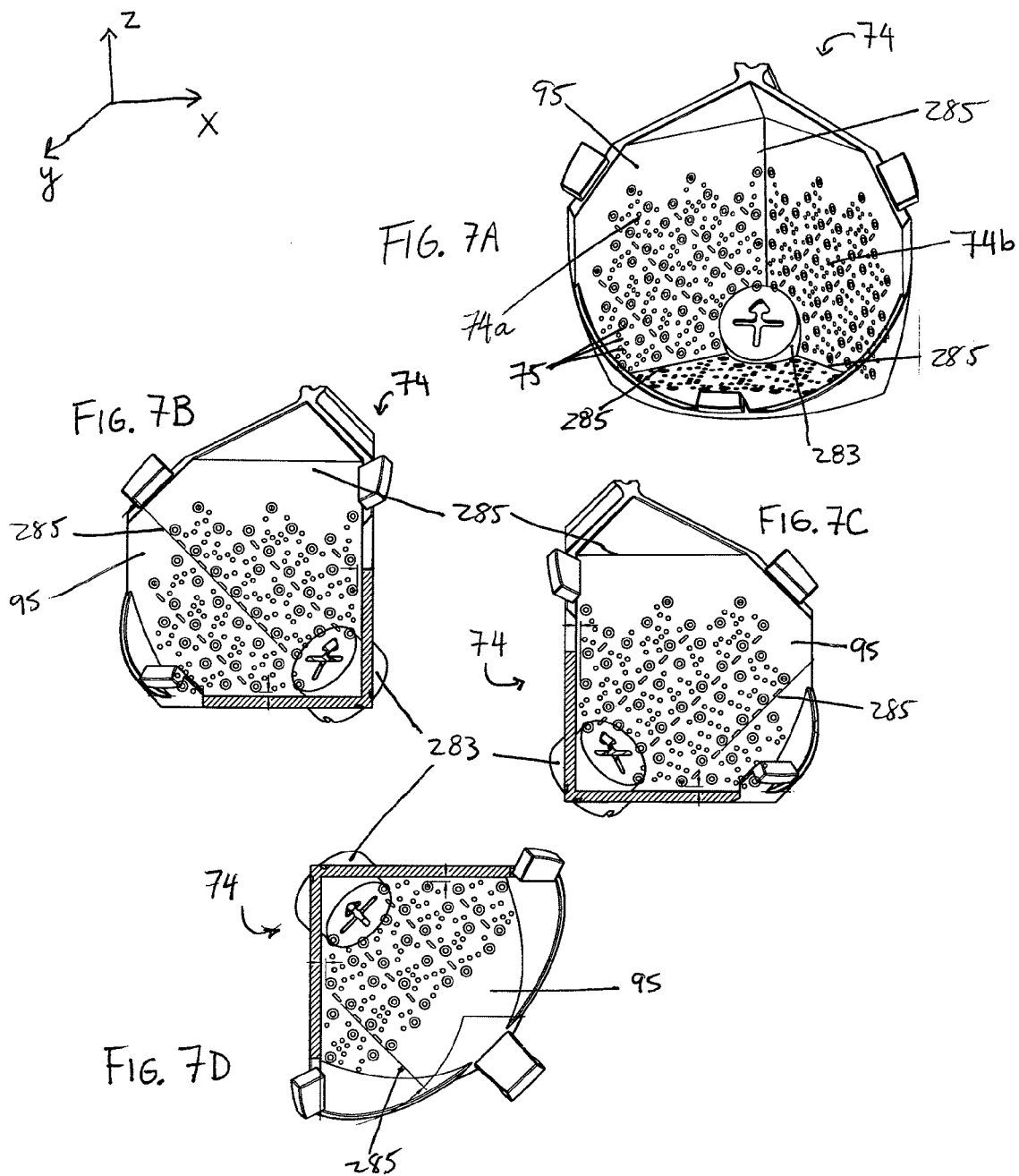

THREE-DIMENSIONAL TARGET DEVICES, ASSEMBLIES AND METHODS FOR CALIBRATING AN ENDOSCOPIC CAMERA

CROSS-REFERENCE TO RELATED APPLICATIONS

This application is related to and claims priority to U.S. Patent Application No. 61/541,427 filed Sep. 30, 2011, entitled "Three-Dimensional Target Devices, Assemblies And Methods For Calibrating An Endoscopic Camera" by Morrisette, et al., the contents of which is incorporated herein by reference in its entirety and for all purposes.

This application is related to U.S. application Ser. No. 12/415,377, filed Mar. 31, 2009, (now U.S. Patent Application Publication No. US 2010/0245541 A1) entitled "Targets, Fixtures, and Workflows for Calibrating an Endoscopic Camera", the full disclosure of which is incorporated herein by reference in its entirety.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery time, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch or less) incisions to provide entry ports for laparoscopic instruments. Laparoscopic surgical instruments generally include a laparoscope or an endoscope for viewing the surgical field.

An endoscope can be calibrated prior to use. In general, calibration is beneficial for many advanced imaging systems, such as advanced computer vision, three-dimensional augmented reality, three-dimensional visualization applications, advanced user interfaces, and image-guided surgery. Such calibration often makes use of a pattern of features that can be imaged by the endoscope to provide calibration data.

Existing calibration devices and methods suffer from a number of problems. For example, properly positioning and orienting the calibration pattern of image features of some prior art calibration targets relative to the imaging device may not be intuitive, and it may therefore be difficult for non-technical persons to obtain the desired calibration. Additionally, since human hands are not very steady, holding the camera or target freehand typically induces motion blur, while having to resort to a large, benchtop endoscopic support might render the system too unwieldy for regular use in the field. Some methods also require manually designating characteristics of the pattern in the resulting images, which may also lead to errors in calibration.

An endoscopic imaging system may also have its color balance (such as white balance) adjusted. In image processing, color balance involves the adjustment of the intensities of colors, typically the red, green and blue primary colors. A goal of this adjustment is to render specific colors correctly, particularly neutral colors. It may also be advantageous to subject an endoscopic-imaging system to diagnostic testing from time to time. A typical endoscopic imaging system includes a variety of components, such as imaging sensors, lens assemblies, etc., that may functionally degrade or fail over time. Where functional degradation that does not rise to an intolerable level has occurred, an endoscopic imaging system may continue to be used due to a lack of knowledge on the part of the user that any functional degradation has occurred. Such latent functional degradation may have significant detrimental consequences in a critical image-guided procedure, such as many minimally invasive surgeries.

While imaging-device calibration, alignment, color balance, and diagnostic testing may be performed by using existing methods and devices, improved methods, devices, and assemblies for performing these tasks in a more convenient and efficient manner remain of interest. For example, methods and assemblies that can be conveniently used to perform some or all of these tasks in a time- and space-efficient manner prior to a surgery, without having to resort to excessive additional training of surgical staff, would be of particular interest.

BRIEF SUMMARY

In accordance with various aspects, improved target devices, assemblies, and methods are provided for generating calibration data, color balance data, and diagnostic data for an imaging device. Such target devices, assemblies and methods can be particularly advantageous when used to calibrate, adjust the color balance on, or run a diagnostic test on an endoscope prior to use. The provided target devices, assemblies, and methods often include a three-dimensional targets surface and can be used, for example, to reduce the amount of time, space, and labor required to calibrate an endoscope, including a stereo endoscope, prior to use. The provided target devices, assemblies and methods may be less prone to errors in the form of accidentally missed steps, and they may result in improved imaging due to image system calibration and color balancing, as well as avoiding the use of a functionally degraded endoscope. Three-dimensional targets, in particular, may facilitate camera calibration using a single image (or pair of images from a stereoscopic endoscope) to reduce the calibration process complexity, calibration time and chance of error as well as allow the efficient calibration of cameras at different focus states.

Thus, the following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some aspects and embodiments of the invention in a simplified form as a prelude to the more detailed description that is presented later.

In accordance with an embodiment, a method for facilitating camera calibration of a stereoscopic endoscope is provided. The method includes engaging the endoscope with a calibration target device to provide a calibration spatial relationship between the endoscope and a target surface of the target device. The target surface extends in three dimensions (for example, with the target surface including intersecting and/or offset planes, a conical or other curving surface, or otherwise not being limited to being disposed along a single plane). A plurality of calibration markers of the target surface are presented to the endoscope while the endoscope has the calibration spatial relationship with the target surface. The presented markers are distributed within a field of view of the endoscope with a first calibration marker extending along a first plane of the target surface and a second calibration marker extending along a second plane of the target surface. The second plane is different from the first plane and asymmetric, relative to the field of view, with the first plane.

The methods for facilitating camera calibration of a stereoscopic endoscope provided herein can involve a number of options. For example, some methods may include configuring an interface of the calibration target device for engagement with the endoscope by selectively positioning a first receptacle of the interface in alignment with the target surface. The engaging of the endoscope with the calibration device may include introducing a distal end of the endoscope into the first receptacle to maintain the calibration spatial relationship. The interface can have a second receptacle alignable with the target surface. The second receptacle can be configured to fittingly receive another endoscope having a viewing angle or cross-section different than the endoscope. Configuring the calibration target device may include moving the second receptacle from alignment with the target surface. A distal end (for example. the objective end or image capture end) of the endoscope may be cylindrical. Each receptacle tapers radially inwardly from an opening toward an inner end of the receptacle to radially engage and position the distal end of the endoscope as the endoscope is inserted into the receptacle.

In other options for camera calibration, the target surface may be supported by a base of the target device, and the movement of the interface relative to the base can be detent indexed. This facilitates the alignment of the receptacles with the target surface.

Each receptacle can have associated an indicium that identifies a characteristic of endoscopes suitable for calibration with the receptacle. The movement of the interface relative to the base can identify the indicium of the receptacle aligned with the viewing surface. A resilient bushing of each receptacle may radially engage the endoscope proximally of the distal end to orient the field of view of the endoscope relative to the target surface. An axial stop of each receptacle promotes axial alignment of the field of view of the endoscope with the target surface.

In variations of the method of calibrating an endoscope, the first plane is offset from the second plane and the first marker is nearer to the endoscope than the second marker. In other variations, the first plane intersects the second plane. The viewed calibration markers can include a third calibration marker extending along a third plane of the target surface. The third plane is different from the first and second planes. The three planes can intersect at a point. A plurality of image markers may be disposed along the first, second, and third planes along first, second, and third planar surface regions of the target surface, respectively. The first, second, and third surface regions may slope away from the endoscope laterally inwardly relative to the field of view of the endoscope so that an inner portion of the field of view presents far viewing markers while an outer portion of the field of view presents near viewing markers to the endoscope. Still other variations may be provided. For example, the fist, second, and third planes may be tangent to the target surface adjacent the first, second, and third markers, respectively, with the target surface curving between the first, second, and third markers along a cone or other three-dimensional curving shape.

The calibration method may further include presenting an orientation feature of the target surface within an inner portion of the field of view. The target device may be manually oriented relative to the endoscope by rotating the target device relative to the endoscope in response to alignment of the orientation feature. The target surface can be white and the orientation feature can include an asymmetric aperture. The asymmetric aperture may be axially offset along the field of view from any hand or other body supporting the target device with a protrusion of the target device near the aperture.

Additionally, illumination may be reflected from the endoscope toward the endoscope with a white color of the target surface surrounding the markers to facilitate white balancing the endoscope. The target surface may comprise a unitary body with laser-printed markers. The markers may differ and each can include a plurality of identification features to allow identification of the differing markers. The markers may have a first tolerance between them. The target surface may float relative to the endoscope with a second tolerance, the second tolerance being looser than the first tolerance.

In accordance with another embodiment, a calibration target device for facilitating camera calibration of a stereoscopic endoscope is provided. The apparatus comprises a target surface having a plurality of calibration markers and a body having an interface configured for engaging the endoscope to maintain a calibration spatial relationship between the endoscope and the target surface such that the markers are distributed within a field of view of the endoscope with a first calibration marker extending along a first plane of the target surface and a second calibration marker extending along a second plane of the target surface. The second plane is different from the first plane and asymmetric, relative to the field of view, with the first plane.

For a fuller understanding of the nature and advantages of the present invention, reference should be made to the ensuing detailed description and the accompanying drawings. Other aspects, objects and advantages of the invention will be apparent from the drawings and the detailed description that follows.

BRIEF DESCRIPTION OF THE DRAWINGS

FIG. 7A shows a perspective view of the calibration target including laser-printed markers along a target surface extending in three dimensions.

FIGS. 7B-7D show left plane, right plane and bottom plane views, respectively, of the calibration target of FIG. 7A.

FIG. 7FB shows a bottom view of the underside of the calibration target.

DETAILED DESCRIPTION

Figure 1:
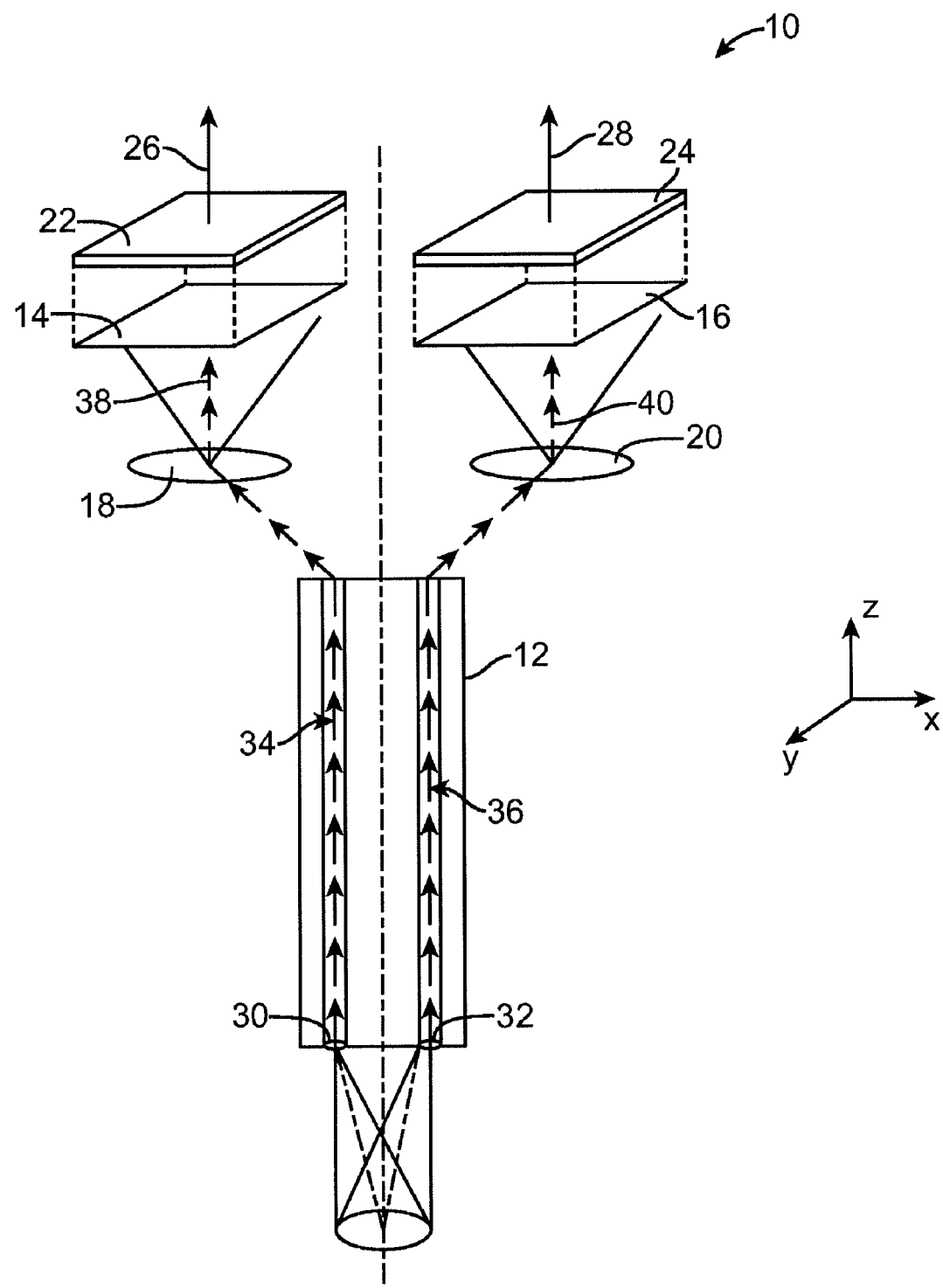
FIG. 1 shows a schematic three-dimensional view of a stereo-imaging system.

In accordance with various aspects and embodiments of the invention described herein, improved 3D target devices, methods, and assemblies are provided for calibration, alignment, color/white balance adjustment, and/or diagnostic testing of imaging devices. Such target devices, methods and assemblies can be particularly advantageous when used with respect to an endoscopic-imaging system prior to use. The calibration facilitated by the devices described herein may include the process of determining intrinsic and/or extrinsic parameters for an imaging device, typically by projecting three-dimensional (3D) points into an image obtained using the endoscope imaging system. The intrinsic parameters may involve the internal geometric and optical characteristics of the imaging device, such as focal lengths in x and y, principal point in x and y, skew and pixel aspect ratio, and/or distortions (often quantified by a few parameters describing the distortions such as radial and tangential distortions). The intrinsic parameters can be used to compensate for imaging errors, such as optical aberrations of the imaging device. The extrinsic parameters may involve the three-dimensional position of the camera reference coordinate system relative to a certain world coordinate system (i.e., six degree-of-freedom pose).

A stereo-imaging device, such as a stereo endoscope, can be aligned prior to use. The alignment process involves adjusting the left and right stereo images horizontally and vertically so as to have zero horizontal and vertical disparity at a certain distance. Fixation disparity is the vertical and/or horizontal misalignment of the eyes when viewing with both eyes (i.e., binocular vision). Without alignment, a viewer's eyes may not properly fuse the left and right images (especially if the vertical disparity is large). Viewing misaligned images can lead to a variety of deleterious conditions including eye fatigue, eye strain and migraines, for example. Exemplary alignment methods and systems are described in commonly owned U.S. Pat. No. 7,277,120, which is hereby incorporated by reference. Calibration parameters for the two imaging paths of a stereo-imaging device can provide parameters (horizontal and vertical offsets) of the alignment process.

The calibration methods and systems described herein often involve imaging a calibration target. The calibration target typically has multiple features having known relative coordinates. An image of the calibration target is processed so as to determine a collection of image coordinates associated with at least some of the target features. Known calibration methods can be used to process the collection of associated coordinates so as to generate calibration parameters, both extrinsic and intrinsic. (For exemplary methods, see Z. Zhang, "A flexible new technique for camera calibration," *IEEE trans. Pattern Analysis and Machine Intelligence,* 2000, volume 22, number 11, pages 1330-1334; and Janne Heikkila and Olli Silven, "A Four-step Camera Calibration Procedure with Implicit Image Correction," available at url www.vision-.caltech.edu/bouguetycalib_doc/papers/heikkila97.pdf, which are both hereby incorporated by reference.) Another method is implemented in a Matlab toolbox by Jean-Yves Bouguet (available at www.vision.caltech.edu/bouguetj/calib_doc/index.html), which is a slightly modified version of the method described in the above listed Zhang reference. Still further calibration and white-balance methods may be described in U.S. application Ser. No. 12/415,377, filed Mar. 31, 2009, (now U.S. Patent Application Publication No. US 2010/0245541 A1), which is also incorporated herein by reference.

Calibration targets can generally be three-dimensional (3D), two-dimensional (2D) or one-dimensional (1D). Calibration using 2D or planar targets generally involves multiple images of the target at different orientations so that the features being imaged have coordinates in three-dimensions.

Imaging Systems

Although embodiments are described with reference to applications in a minimally invasive surgical system employing an image capturing device in the form of an endoscope, it is to be understood that the field of the invention is not necessarily limited to these applications. For example, embodiments can be used to calibrate imaging devices in general.

Referring to the drawings, and with specific reference to FIG. 1, an imaging system, in accordance with embodiments, is generally indicated by reference numeral 10. System 10 includes a stereo imaging device in the form of a stereo endoscope 12, for example. The system 10 further includes two Charge Coupled Devices (CCDs) 14 and 16, optical lenses 18 and 20, and read means 22, 24 for reading the CCDs and converting information read on the CCDs into a digital format. The read means 22, 24 is typically an appropriate electronically driven system such as a Camera Control Unit (CCU) that transforms optical information read from the CCDs 14, 16 into digital format. The CCD and CCU arrangements can be of the type available from Panasonic™. under the part nos.: GP-US522/GP-US532 3CCD color CCU. Accordingly, an electronic processor (not shown) is typically in operative communication with the read means 22, 24 as indicated by lines 26, 28. Optical lenses 30, 32 are disposed at a distal viewing end of endoscope 12. Images are passed through the lenses 30, 32, are passed along optical paths indicated by arrows 34, 36 in endoscope 12, are magnified through lenses 18, 20 and are then projected onto optically sensitive surfaces of the CCDs 14, 16, as indicated by arrows 38, 40. Although imaging system 10 is shown and described, it will be appreciated by one skilled in the art that various alternative imaging systems can alternatively be used.

Calibration Assemblies

Figure 2:
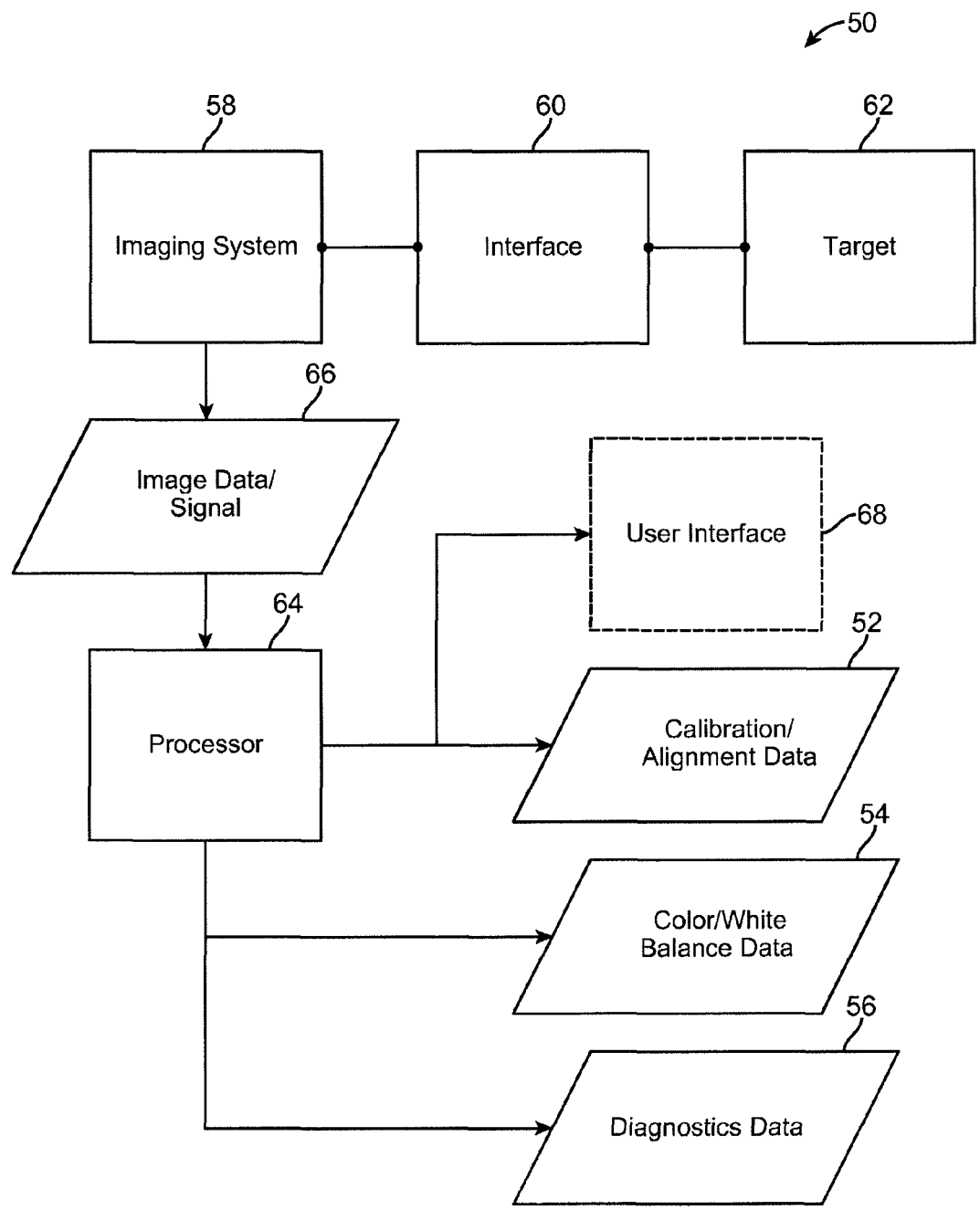
FIG. 2 diagrammatically illustrates a calibration assembly and an imaging system.

FIG. 2 diagrammatically illustrates a calibration assembly 50 that can be used to generate calibration/alignment data 52, color/white balance data 54, and/or diagnostics data 56. Calibration assembly 50 includes an imaging system 58, an interface 60, a target 62, and an electronic data processor 64. Imaging system 58 can include any number of devices, such as a stereo endoscope, that can be used to capture an image and output image data or an image signal in response thereto. Interface 60 provides a means by which to constrain the imaging system 58 relative to the target 62. Interface 60 can include, for example, a lock or other mechanical constraint to prevent relative motion between the imaging system and the interface. Interface 60 can be coupled with target 62 so that the target is posed (positioned and oriented) relative to the constrained imaging system 58 so that the target is within the field-of-view of the imaging system. In some embodiments that will be described in more detail below, the interface 60 and target 62 are coupled so as to form a calibration fixture. Processor 64 is coupled with imaging system 58 so as to receive the image data/signal 66. Processor 64 uses the image data/signal 66 to generate calibration/alignment data 52, color/white balance data 54, and/or diagnostic data 56. Calibration/alignment data 52 can include unique correspondences between extracted image features and features of target 62.

Calibration assembly 50 can include additional optional components. For example, the interface 60 and the target 62 can be coupled by way of a motorized mechanism. The motorized mechanism can be driven so as to be synchronized with the capture of images, such as by rotating the target relative to the interface between image captures and stopping during an image capture. The motorized mechanism can also be synchronized with the focus of the imaging system 58. It has been observed that camera calibration parameters can differ when the focus is changed. As such, an imaging system may need to be calibrated at multiple focus settings. In this circumstance, even more images will need to be taken and a motorized mechanism may be of even greater benefit in reducing the workload on a human operator. Interpolation can be used to determine calibration parameters in between the calibrated focuses.

Calibration assembly 50 can include an optional user interface 68. User interface 68 can be used to guide a human operator during the image capture process. The user interface can include a communication device, such as a display or speaker, that can be used to guide the operator to position the target relative to the imaging system. For example, user interface 68 can be used to guide the operator to rotate the target relative to the imaging device by a certain angle, such as by showing the current orientation and the desired orientation. The user interface 68 can inform the operator to keep the image device fixed relative to the target during image capture so that no motion blur occurs, which can be especially important during modular transfer function (MTF) estimation where motion blur may not be discernible from the blur due to the optical system.

Target Device

Figures 3A, 3B:
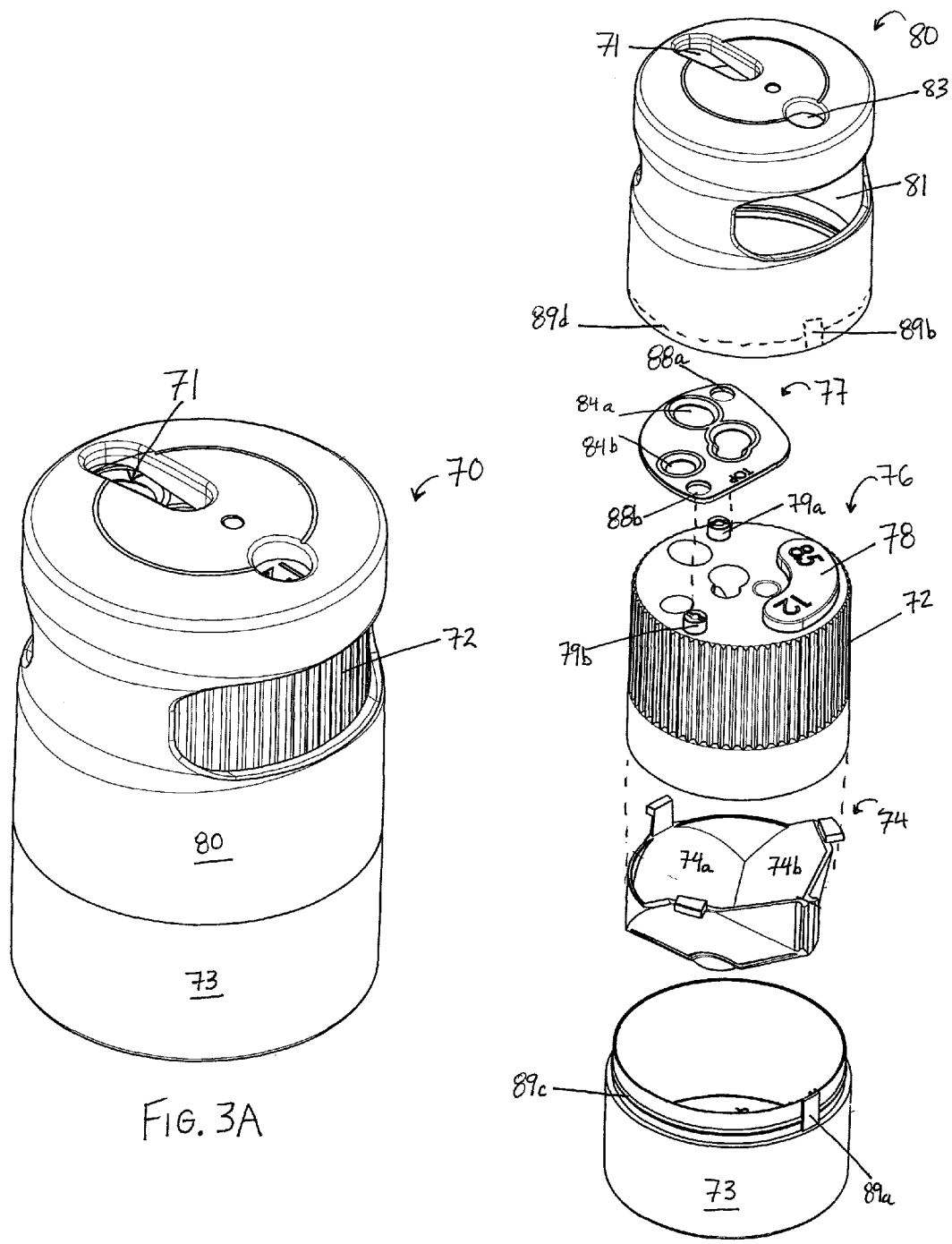
FIG. 3A shows a perspective view of the 3D calibration target device.
FIG. 3B shows an exploded view of the 3D calibration target device.

Referring now to FIG. 3A, a three-dimensional calibration target device is generally indicated by reference numeral 70. An opening 71 can separately receive any one of at least two and preferably four or more different types of endoscopes of varying sizes and shapes, including endoscope 12 shown in FIG. 1, for example. The size of the endoscope is selected by rotating the thumb dial 72 which rotates receptacle 84a or 84b into alignment with opening 71. Indicia 78 (inscribed "8.5" and "12" in this example) indicate the alignment of receptacles 84a or 84b with the opening 71. The indicia correspond to the endoscope size acceptance (8.5 mm and 12 mm, in this example). When inserted, the distal end (i.e. image-capture end or) of an endoscope passes through opening 71 and is received by receptacle 84a or 84b (as selected by the user) and is held in place by receptacle 84a or 84b. Resilient bushings or the like may be placed around the opening 71 and/or the open ends of receptacles 84a and 84b to allow additional support to the endoscope when inserted.

FIG. 3B is an exploded view of the 3D calibration target device 70. Target device 70 includes a base 73 and a 3D target body 74, with the target body including a target surface that extends in three dimensions, such as along panels 74a and 74b which are located along different asymmetric planes relative to the field of view as seen through the endoscope. As more specifically described with reference to FIGS. 1-9 and 12-13, markers of the target device may be YAG laser-printed directly onto the material from which target body 74 is molded, may be printed onto stickers that are adhered to the target body, or may otherwise be positioned on the target surface of the target body. The makers may include, but are not limited to, primitives (e.g. dots) or the like. The markers can be grey, although black or other colors that contrast with a white (or relatively light) background sufficient for viewer discrimination can also be employed. An insert molded interference plate 77 is secured to the calibration fixture (aka scope holder) 76 by two detent pins 79a and 79b that dock the lid 80 to the base 73. It is appreciated that other means of attachment may be used to secure the lid and base to enclose the other components of the 3D calibration target device 70, such as adhesive bonding, fasteners, ultrasonic welding, or the like. An opening 81 in the lid 80 provides access to a textured thumb dial 72 when assembled so as to facilitate rotational selection of a desired receptacle. The size indicator window 83 allows a view of the indicium 78 that correspondingly indicates openings 84a or 84b selected by rotating the thumb dial 72.

Figure 4C:
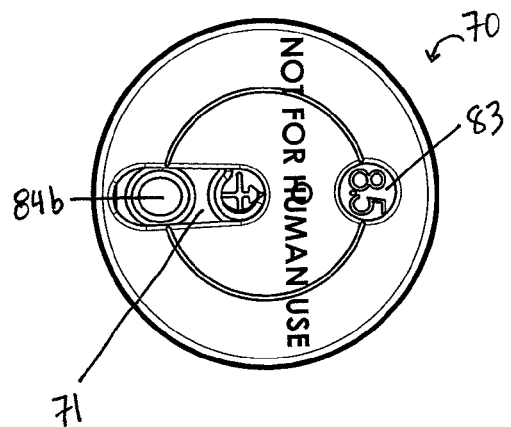
FIG. 4C shows a top view of the 3D calibration target device adjusted in position to receive a 8.5 mm endoscope.
Figure 4B:
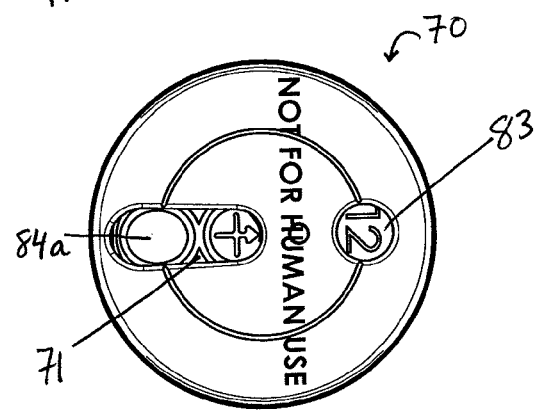
FIG. 4B shows a top view of the 3D calibration target device adjusted in position to receive a 12 mm endoscope.
Figure 4A:
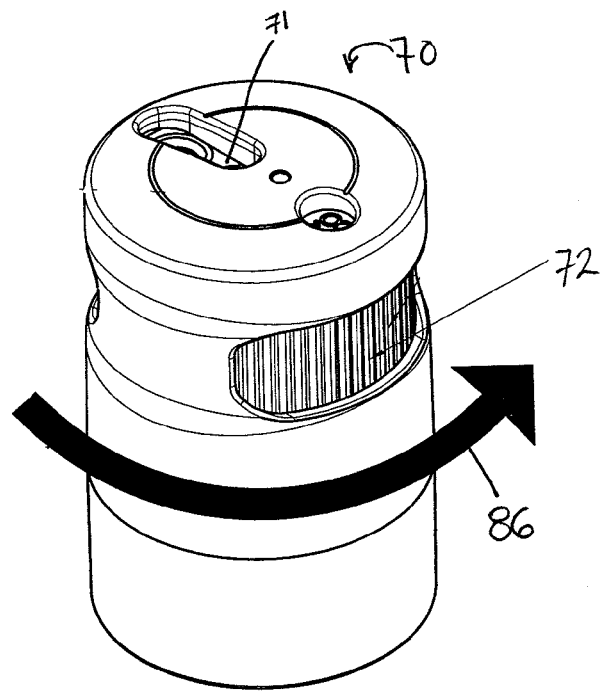
FIG. 4A shows a perspective view of the 3D calibration target device with the directional movement of the interface relative to the base indicated.

As shown in FIG. 4A, the thumb dial 72 smoothly rotates in the direction shown by arrow 86 between locking detents 79a, 79b (FIG. 3B). The locking detents between the lid 80 and calibration fixture 76 prevent the scope holder from being inadvertently rotated while it is engaged with an endoscope. The detents facilitate alignment of the receptacles with the target surface. The detents also lock the spatial relationship between the scope and the calibration target to prevent their inter-motion during the image data acquisition of multiple focus positions.

FIG. 4B shows a top view of the 3D calibration target device 70 including the size indicator window 83 showing "12" to indicate that a 12 mm endoscope is currently selected. FIG. 4C shows a top view of the 3D calibration target device 70 including the size indicator window 83 showing "8.5" to indicate that an 8.5 mm endoscope is currently selected. As appreciated when FIGS. 4B and 4C are compared, the opening 71 remains the same size but the size of the receptacles 84a and 84b corresponding to 12 mm and 8.5 mm, respectively, change.

Figure 5:
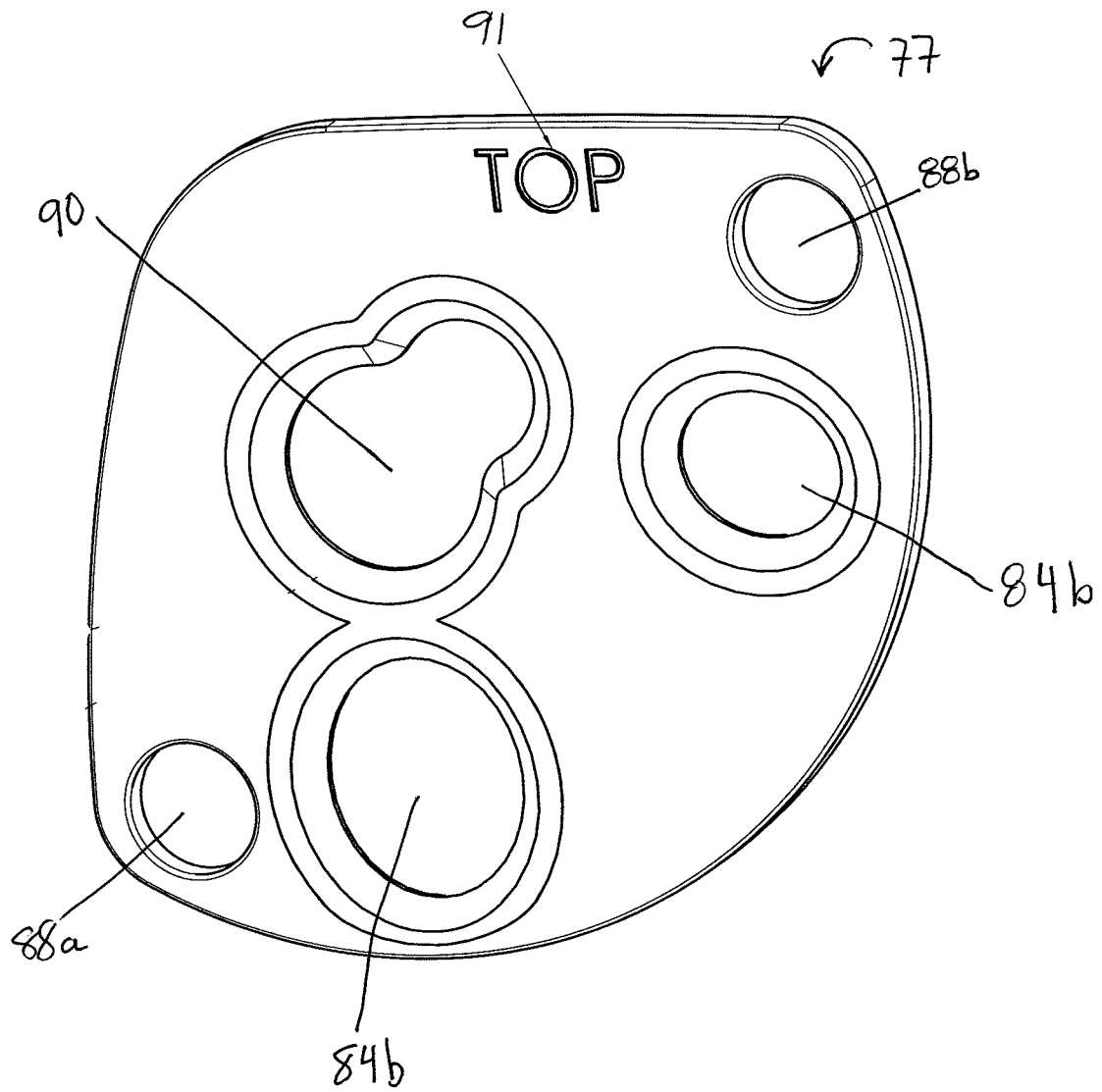
FIG. 5 shows a perspective view of the interference plate of the 3D calibration target device.

FIG. 5 shows a perspective view of the interference plate 77 component of the 3D calibration target device. The interference plate 77 includes alignment features 88a and 88b to ensure plate 77 is in the correct right/left orientation with respect to the openings 84a and 84b shown in FIG. 3B. Inscription 91 assists with top/bottom orientation when plate 77 is positioned on top of calibration fixture 76 during initial assembly or during reassembly after cleaning or servicing, for example. The interference plate holds the endoscope steady during the calibration scan process. The interference plate is particularly helpful in preventing movement when the endoscope and calibration device are hand held. A body of interference plate 77 may be molded, machined, or the like, of a relatively rigid plastic, and resilient polymer bushings may be insert molded around openings 90, 84b so as to resiliently engage and center an endoscope inserted therethrough.

Figure 6A:
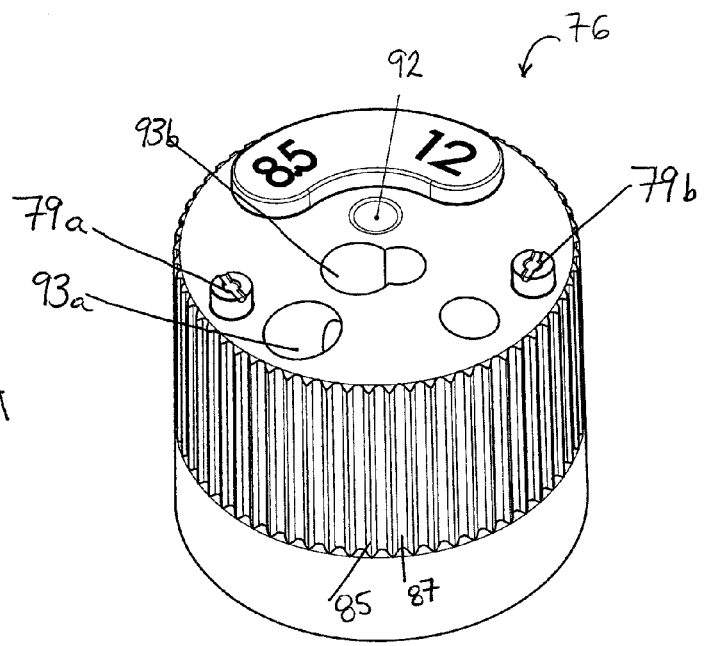
FIG. 6A shows a perspective view of the calibration fixture including a dimple gate.

FIG. 6A shows an alternative perspective view of the calibration fixture 76 including a dimple gate 92. The calibration fixture has an interface (i.e. endoscope holder) for constraining engagement with the endoscopic imaging system and provides alignment between the endoscope and a target body 74 rotatably coupled with the interface so that a target surface of the target body is within the filed of view. Rotation of the calibration fixture 76 relative to the target body reconfigures the target device by selecting which receptacle or receptacles of the fixture are aligned (and hence which size endoscope can be aligned) in a desired spatial arrangement with the target surface.

Figure 6B:
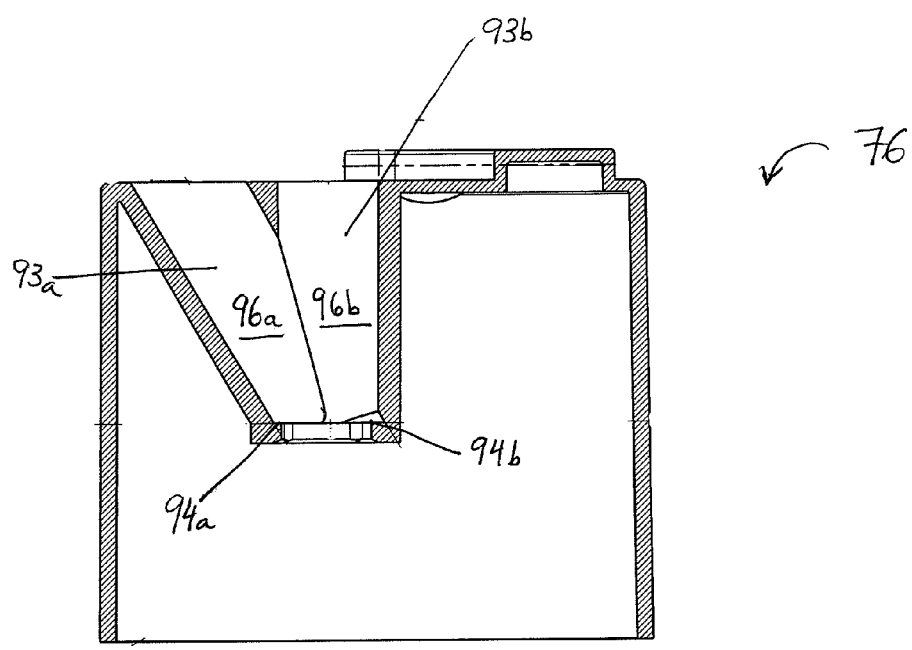
FIG. 6B shows a cross section view of the inspect feature of the calibration fixture.

FIG. 6B is a cross-sectional view of the calibration fixture 76 shown in FIG. 6A that can be used to provide constraining engagement with an imaging device, such as a zero-degree (i.e. straight) or 30-degree endoscope. The basic functionality of calibration fixture 76 can be provided in a number of ways. For example, calibration fixture 76 can be configured as an integral unit having multiple integrally formed receptacles, or calibration fixture 76 can be fabricated from a number of subassemblies. Regardless of the chosen fabrication choice, calibration fixture 76 includes receptacles 93a and 93b shaped to interface with a 30-degree or straight endoscope, respectively. As previously mentioned, 8.5 mm or 12 mm sizes of each endoscope can be selected by rotating fixture 76 relative to the other components of the target device. Once positioned for an 8.5 mm endoscope, either a straight 8.5 mm diameter scope can be inserted into receptacle 93b, or a 30-degree 8.5 mm diameter scope can be inserted into receptacle 93a. Similarly, when positioned for a 12 mm scope, either a straight 12 mm scope or a 30 degree 12 mm scope can be inserted. Thus, a total of 4 different endoscopes of differing size and angle can be separately selected in this particular embodiment. Although receptacles 93a and 93b can be cylindrical, other non-cylindrical configurations can be used. Axial stops 94a and 94b may act as "bumpers" to position the scope along the axis of the receptacle so as to provide a desired focal range between the endoscope and the target surface, and to prevent the endoscope from being inserted too far into the calibration fixture 76 and thus too close to the target. Alternatively or additionally, the diameter of the channel 96a and/or 96b of receptacles 93a and/or 93b may be inwardly tapered or beveled to axially position the distal end of the endoscope relative to the target surface when the endoscope is inserted into the appropriate receptacle of the calibration fixture (aka scope holder) 76.

Figure 7E:
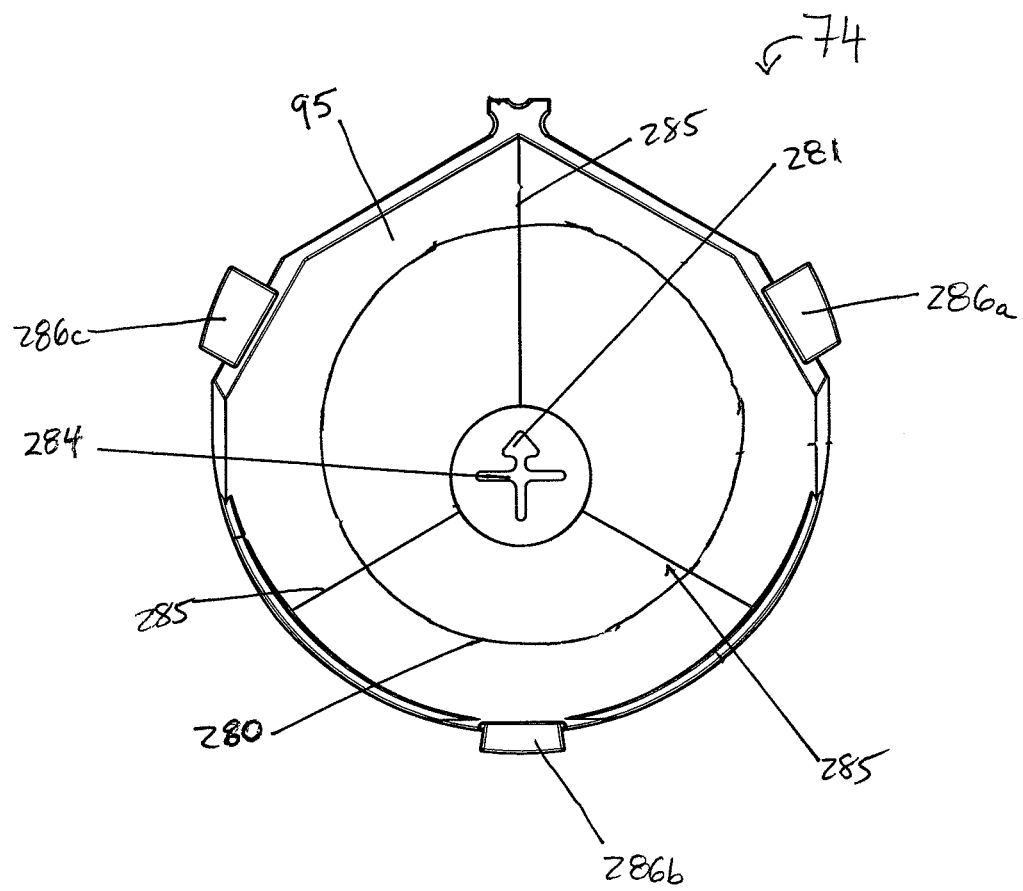
FIG. 7E shows a top view of the calibration target without markers.

FIG. 7A depicts a 3D target body 74 in accordance with an embodiment of the subject invention. The 3D target 74 is constructed of a single cast mold with at least two different panels 74a 74b located disposed along different asymmetric planes. The panel edges 285 and tabs 286a-286c shown in FIG. 7E, the latter of which facilitate attachment of the target 74 to the base 73 (FIG. 3B). Different perspective views of target 74 are shown in FIGS. 7B-7D from inside the field of view of the endoscope when attached to the calibration target. Target 74 of FIG. 7A is a perspective view that includes a target surface 95 on which target features, local groups of which can be used as markers 75, are located in various patterns on each panel. Target surface 95 can directly incorporate the target features by laser printing or another similar process, or a target containing target features can be mounted on or otherwise affixed to target surface 95. The calibration target can be designed for a single use/disposable application or a reusable application. If the target is reusable, the markers will preferable be formed on metal or similar material so as to withstand repeated sterilizations without excessive fading, for example.

Figure 7F:
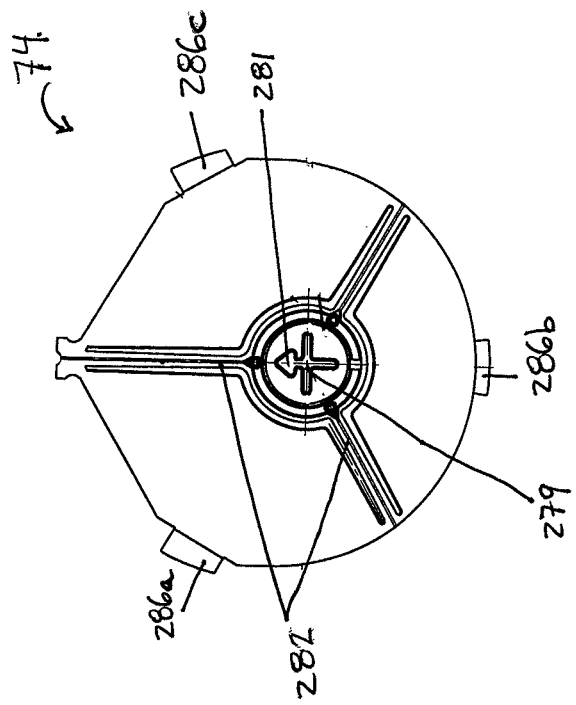
FIG. 7FA shows a perspective view of the underside of the calibration target.
Figure 7F:
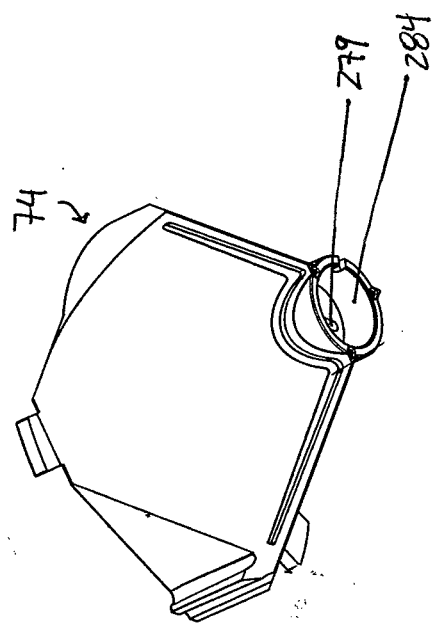
Figure 7G:
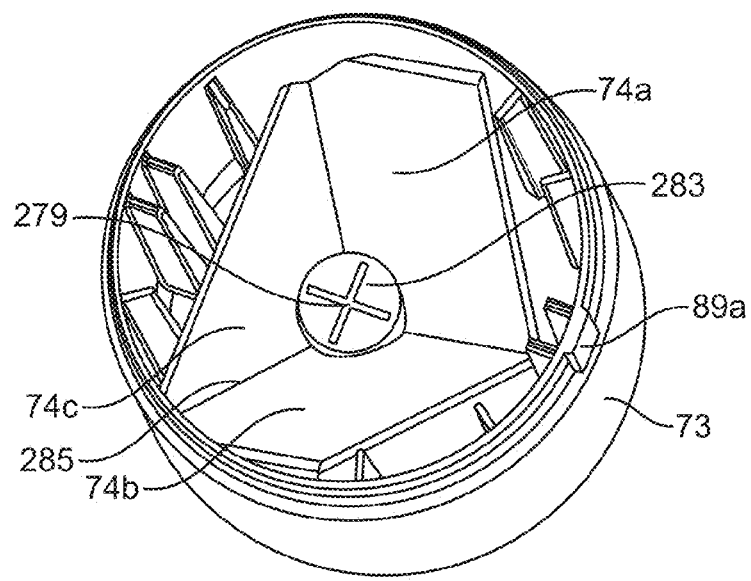
FIG. 7G shows a perspective view of the part of the calibration target where the calibration features sit.
Figure 7H:
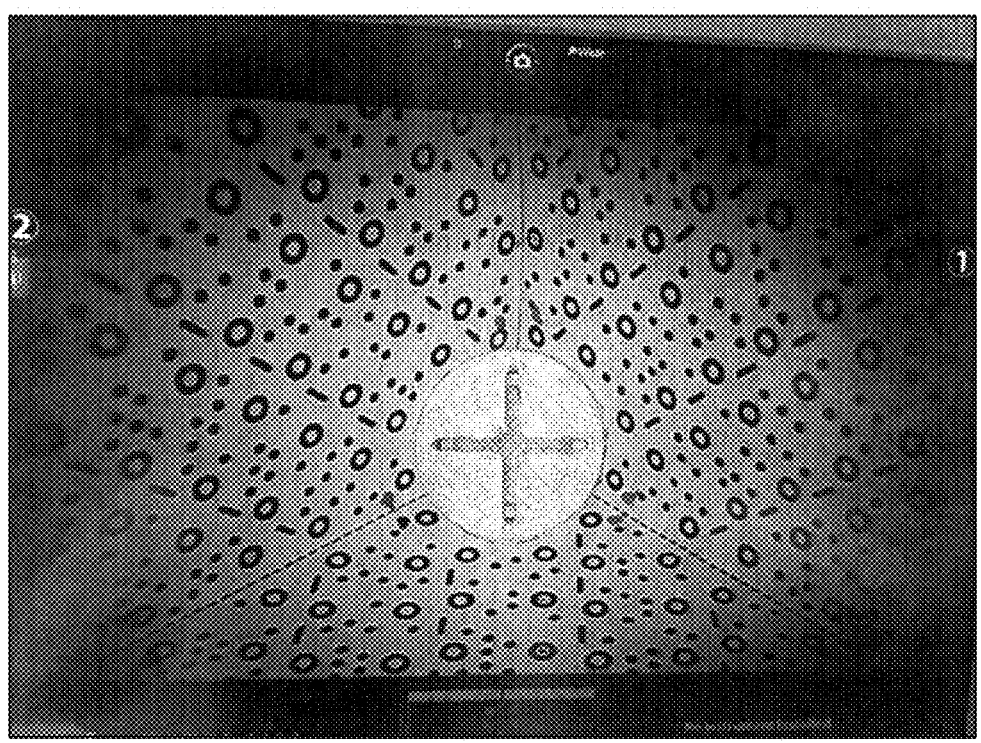
FIG. 7H shows a perspective view of the calibration target as seen from the camera.

FIG. 7E shows a top view of the calibration target 74 (without markers). A portion of the upper surface of target 74 would be seen by the endoscope so as to included within a field of view 280 (shown here schematically) of the endoscope 12 when the endoscope is attached to the calibration target device 70. FIG. 7FB is a bottom view of target 74 showing that the target includes a crosshair 279 and mold seams 282. The crosshair 279, positioned in a central portion of the target 74 as seen in the field of view of the endoscope, may contain an arrow 281 on one end. Crosshair 279 can be used for XY alignment of left and right channels of the stereoscopic endoscope, while the arrow can be used to help rotationally align the endoscope with the calibration target device. More specifically, the cylindrical distal end of the endoscope can be introduced into the receptacle, and the target surface (and crosshair 279) can be imaged by the endoscope and the image can be displayed to the user. The target device can then be rotated about the cylindrical end of the endoscope (or vice versa) until the crosshair has a desired orientation in the displayed image, such as with the arrow pointed upward. A variety of alternative asymmetric shapes might be employed.

Figure 15A:
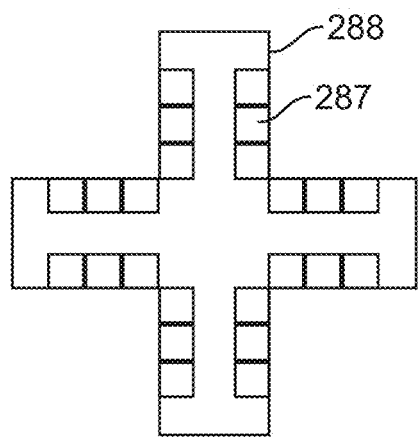
FIG. 15A diagrammatically illustrates a crosshair pattern encoding information using gray fill blocks.
Figure 15B:
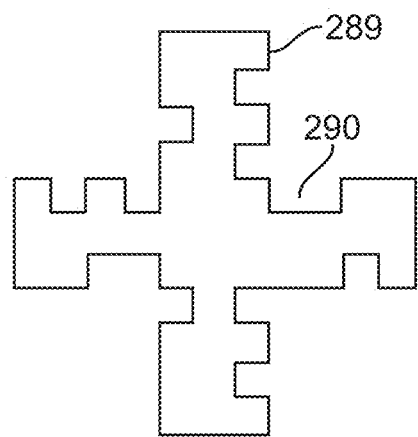
FIG. 15B diagrammatically illustrates a crosshair pattern encoding information using light and dark areas.

In other embodiments, crosshair configuration 288 shown in FIG. 15A may encode information in the form of a "skeletal" crosshair with grey-fill areas 287. The grey fill areas may be used as binary machine-readable features, being turned on or off as desired by the user by filling them in or leaving them blank to provide information to the endoscope system being calibrated using the calibration device. Such information may include, but is not limited to, date of manufacture of the calibration device, type of calibration device, serial number and version number of the calibration device, for example. In an exemplary embodiment, the crosshair pattern, including light 290 and dark 289 areas, may encode similar information in the configuration shown in FIG. 15B, or with the grey-fill areas 287 in a different combination of light and dark regions in any desired combination so as to provide information analogous to that provided by bar codes, radio frequency identification (RFID tags, Bokode, Quick Response Codes (QR Codes) and other types of information.

The crosshair may comprise a cut out or aperture 284 (FIG. 7E) to allow light to pass through and contrast with the target background surface material. It may also be positioned on a raised pedestal 283 (FIGS. 7A-7D) with the bottom surface of target 74 having a protruding feature such as cup wall 284 (FIG. 7FA) extending away from the target 74 near aperture 279 so as to prevent the aperture from being filled by a hand of an operator or other structure and thereby to improve contrast, for example.

Figure 16:
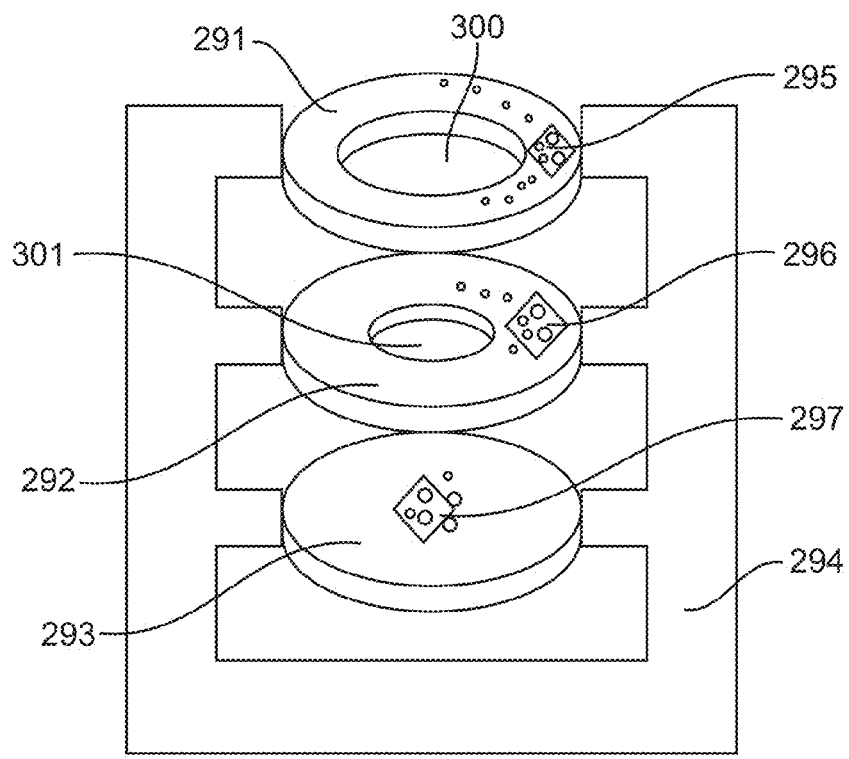
FIG. 16 schematically shows an alternative target configuration of a target surface.

In an additional embodiment shown in FIG. 16, the 3D target can be configured to take the form of markers and/or visual features disposed along planes that are generally parallel to each other. The target surface and makers can be formed on a stack of panels that can be various shapes including square, rectangular, circular or oval (as in this particular example). Holes 300, 301 in the panels closer to the imaging device provide light and allow viewing of those panels farther away from the imaging device. The openings decrease in size the farther they are from the receptacle and viewing end of the imaging device. The oval-shaped discs 291, 292, 293 are vertically stacked and attached to a mounting 294 as shown in FIG. 16. In other embodiments, the panels may have sufficient transparency to allow viewing of markers through intervening panels by the imaging device and therefore may not have openings. Acceptable transparent materials may include glass or clear plastic, for example. Regardless of the panel material employed, self-referential markers 295, 296, 297 may be included on each panel for calibration purposes according to the method illustrated in FIG. 11, for example.

Figure 17:
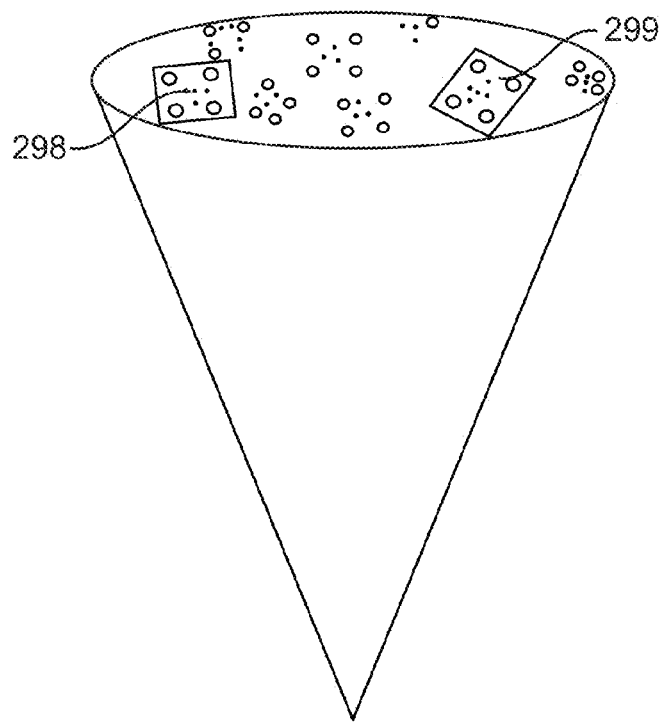
FIGS. 17 schematically shows a s yet another alternative target configuration of a target surface.

FIG. 17 is a perspective view of yet another embodiment having a conical 3D target configuration. Truncated cones may also be used. Markers are shown in several positions 298, 299 on the inside surface of the cone, with each marker generally extending along a plane that is tangent to the curving surface of the cone. These markers can be used to calibrate an imaging device using the method shown in FIG. 11. Various other target configurations could also be used, so that the target device need not necessarily be limited to the specific target configurations described herein.

Figure 14A:
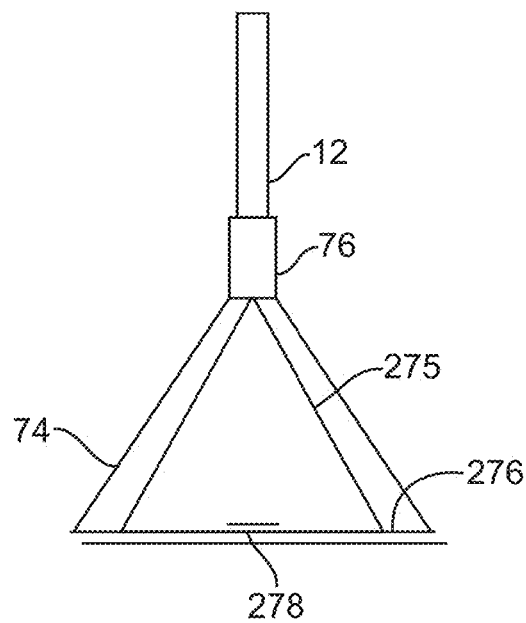
FIGS. 14A and 14B are schematic cross sectional diagram showing size reduction of the calibration target with and without using optical path folding from a reflective material, respectively.
Figure 14B:
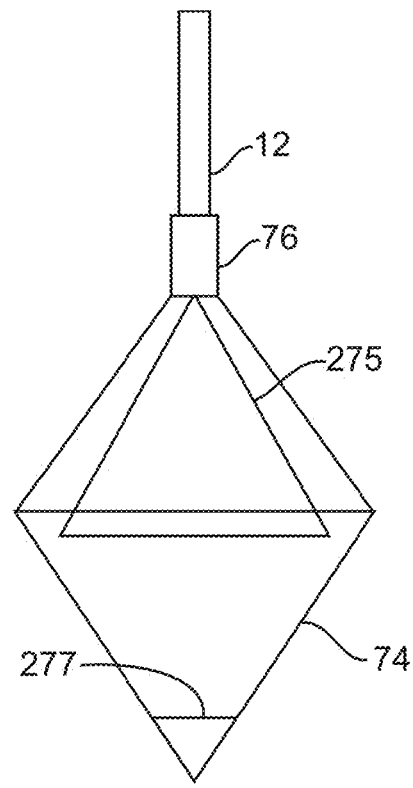

The size of the target may optionally be decreased by including lenses and/or mirrors to alter the optical path between the endoscope 12 and the target surface 275. Specifically, in an embodiment of the subject application, the size of the target can be reduced using a mirror 276 shown in FIG. 14A, resulting in a smaller volume target device as compared to an otherwise optically similar target device that does not include a minor (as shown in FIG. 14B). The visual feature 278 for scope alignment in FIG. 14A lies in closer proximity to the endoscope 12 and calibration fixture 76 as compared to the visual feature for scope alignment 277 and 279 in the embodiments of FIGS. 14B and 3A-7F. The camera field of view 275 of the target surface could otherwise remain unchanged in these examples.

The receptacle of fixture 74 constrains target motion in six degrees-of-freedom (three-dimensional rigid transformation, three for translation and three for rotation) to 1 degree-of-freedom rotation. This makes control of the target much more straightforward. The constrained motion can also guarantee that sufficient data is obtained for a successful camera calibration by following simple procedures (for example, by rotating the fixture until an image from the scope shows aperture 279 in a desired orientation, such as with the arrow pointed upward). The use of a calibration fixture decreases dependence upon the user and enhances the repeatability of the calibration process. This is especially advantageous with surgical assistants who may know little about camera calibration.

Target Designs

A variety of different target designs can be used with aspects of the calibration assemblies described herein, such as with calibration assembly 50 of FIG. 2. Preferably, a target design incorporates a self-referential pattern of target features so that the image can be automatically processed without the need for any manual designation. More preferably still, the target design incorporates multiple discrete self-referential patterns (i.e., markers). A self-referential pattern can include, for example, localizer features and identification features. Localizer features provide positional or orientation information to determine pose/alignment of the marker and the identification features can be used to differentiate between different markers. Such multiple self-referential patterns can advantageously provide for more robust calibration image processing by being more tolerant of partial occlusions and/or image misalignments.

The use of multiple self-referential markers provides a number of advantages. One advantage is that portions of the image containing different markers can be separately processed, which can add a level of robustness to the processing of the overall image by allowing the collection of at least some useable data where portions of the target are not imaged or portions of the image cannot processed for some reason. Another advantage is that the target pattern may allow for the use of a less complex calibration fixture, especially with respect to calibration of a thirty-degree endoscope that may image different portions of the target depending on its relative orientation to the calibration fixture. Another advantage is that a marker can be configured to occupy a small area, which is less affected by non-linear distortion as compared to a larger pattern.

Using self-referential markers to discriminate features removes the need for manual interaction for model-image feature association and minimizes the assumptions on the filed of view and viewing orientation of the target so that it is ready to be used by cameras of different parameters. The redundancy embedded in the self-referential features increases the overall robustness of the calibration method.

Figure 8:
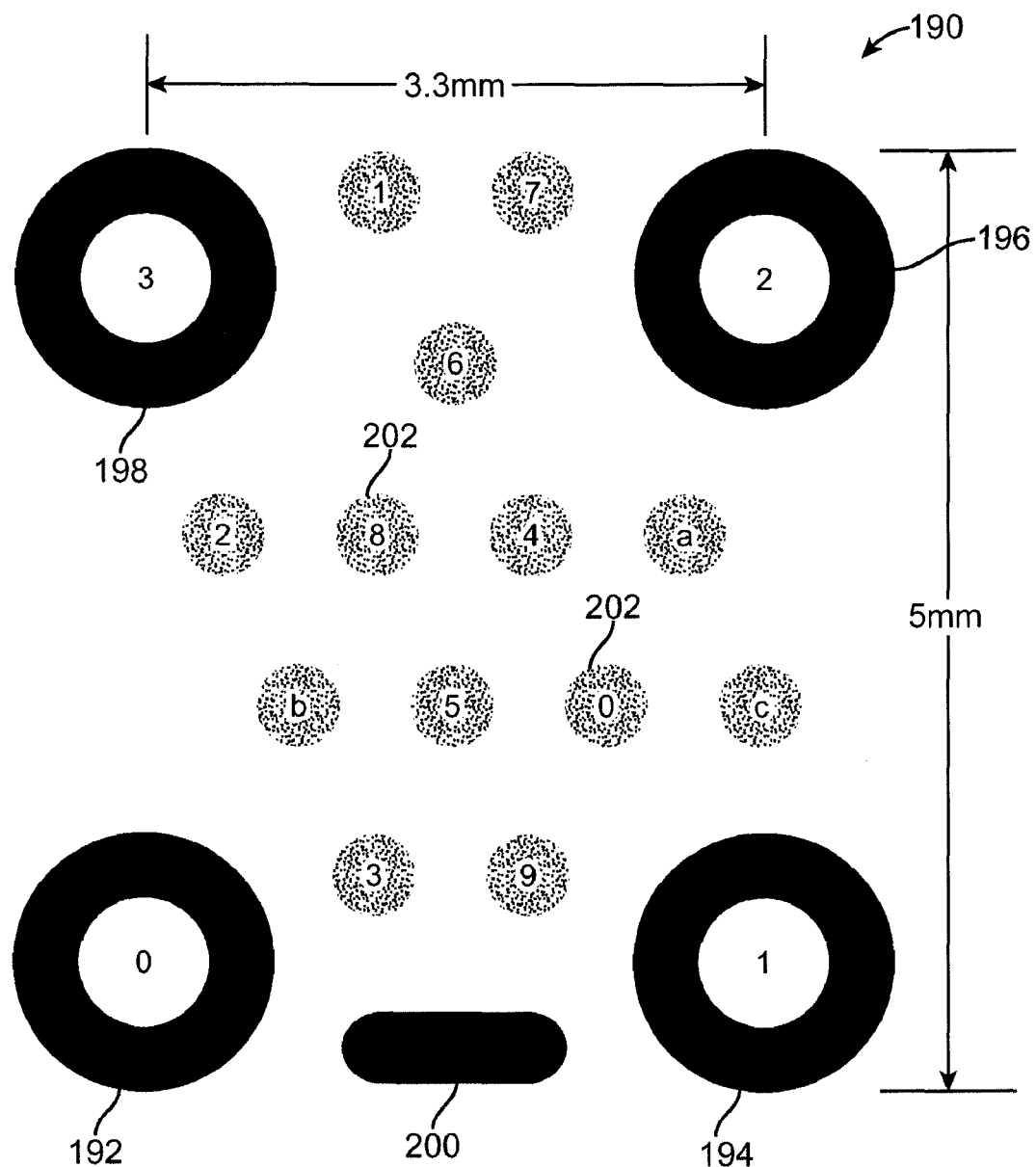
FIG. 8 diagrammatically illustrates a two-dimensional marker having localizer features and identification features.

FIG. 8 diagrammatically illustrates a two-dimensional self-referential marker 190 having localizer features and identification features, in accordance with an embodiment. The localizer features include four dark circles 192, 194, 196, 198 and a dark bar 200. The numbers within the circles are illustrative of position designations. The localizer features of a particular marker can be automatically associated with resulting image features, which allows for the association of the know target relative coordinates of the localizer features with their image coordinates.

The identification features of marker 190 include thirteen dots 202 (i.e., bits). The presence or absence of a dot at a particular location in the designated pattern is a binary indicator (e.g., if the dot exists is signifies a binary "1" for the value associated with that dot's position, and if the dot does not exist it signifies a binary "0" for the value associated with that dot's position). Accordingly, in the illustrative FIG. 8 example, the values shown ("0" through "9" and "a" through "c") are illustrative of position designations for one or more binary numbers. The thirteen dots 202 can be segregated, with some dots being used for identification data and some dots being used for error checking data. The presence or absence of the dots used for identification data can be used to designate a number of unique codes (or identifications). The presence or absence of dots used for error checking data can be used to validate a code or identification determination. In one presently preferred approach, the thirteen dots are segregated into six dots used to carry identification information (resulting in 64 unique codes), with the remaining seven dots used for error checking. Among the seven error checking dots, six can be set to be the inverse of the identification dots, and the remaining dot can be used as checksum data. The rationale for this approach is to always ensure that there are six or seven dots that are physically present in a pattern (i.e., they are set to one). This avoids an all-zero (all blank) pattern as a valid code and provides alternative features that can be used to provide positional information if required. The specific identification feature pattern illustrated (e.g., number and position of dots), along with the illustrated manner in which identification feature information is coded (e.g., the use of dots), is an example of many possible identification features (see e.g., other exemplary patterns described below). For more information regarding self-referential markers, see the commonly owned U.S. Patent Application Ser. No. 61/204,084, filed Dec. 31, 2008, entitled "Fiducial Marker Design and Detection for Locating Surgical Instrument in Images," which is hereby incorporated by reference.

Figure 9A:
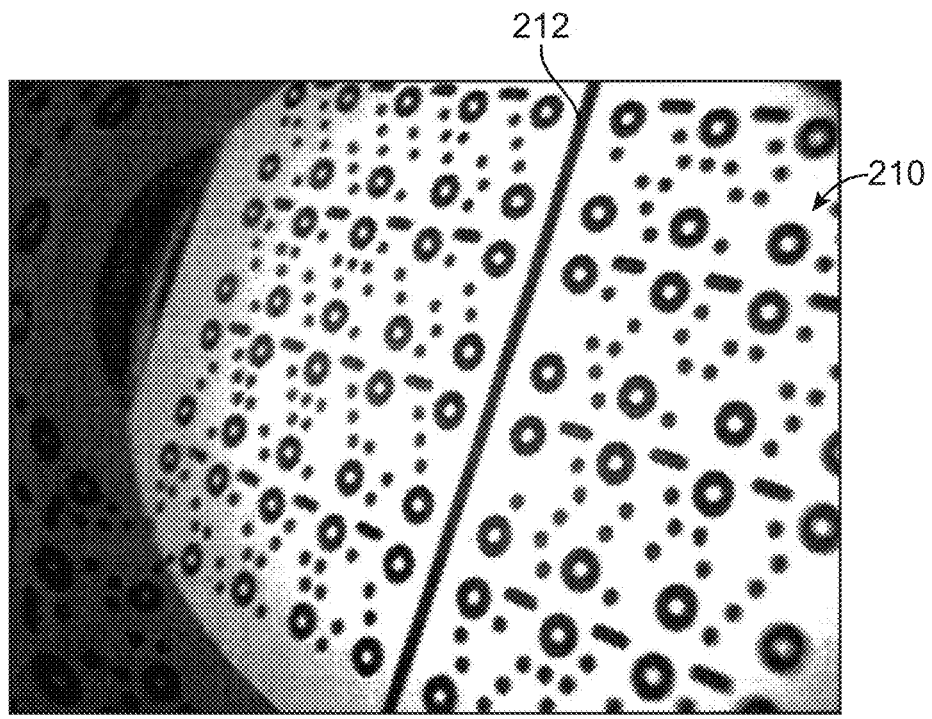
FIGS. 9A-9B show respective images from two different viewing directions of a calibration target having multiple two-dimensional markers and a slanted-edge modulation transfer function (MTF) feature.
Figure 9B:
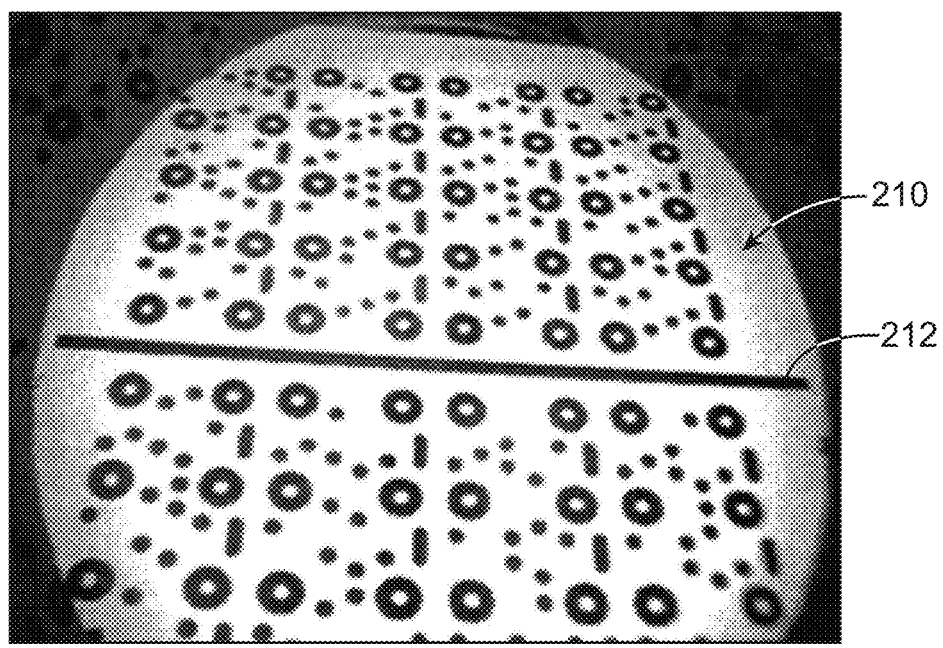

A target can include multiple self-referential markers. FIGS. 9A and 9B are two different images of a target 210 containing multiple self-referential markers, in accordance with an embodiment. The images were obtained using a calibration target device 70 and calibration fixture 76 in accordance with FIGS. 3A and 6B. The imaged target 210 includes two groups of sixteen markers, with the groups separated by a straight dark bar 212 that can be used as a slanted-edge MTF feature. The markers and the dark bar 212 are set against a white background that can be used for the determination of a color/white balance adjustment for the imaging system. A portion of an image of a particular marker can be separately processed so as to determine image coordinates for one or more of the localizer features of the marker, and to determine the identification of the marker so that the target relative coordinates of the marker localizer features can be associated with their image coordinates for use in determining calibration/alignment data for the imaging system. As discussed above, the positions of the marker dots in the images can also be used to formulate coordinate information for use in the generation of calibration/alignment data. It can be seen from FIGS. 9A and 9B, for example, that each of the markers has a different set of dots showing in the pre-designated pattern. It can also be seen that some of the markers share localizer features, with some circles being used as a localizer feature for two markers. The visual features are composed of patterns that are self-discriminative. For example, a pattern can be differentiated from other patterns by itself or over a small area without the need to analyze all the patterns in the field of view.

Image Processing

Figure 10:
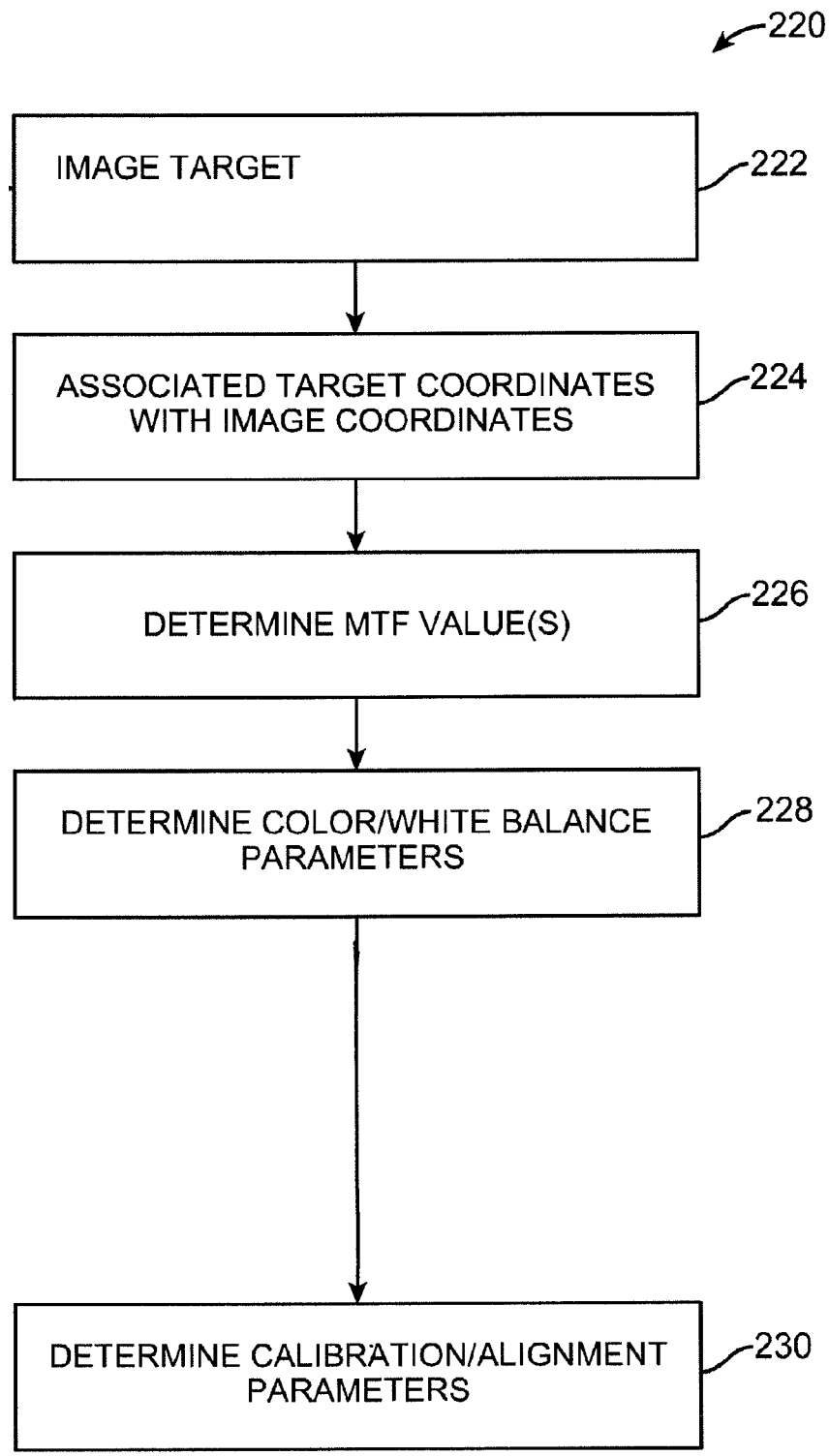
FIG. 10 is a flow diagram for a method for determining MTF value(s), color/white balance parameters, calibration parameters, and alignment parameters.

Modulation Transfer Function (MTF) characterizes the sharpness of an imaging system. FIG. 10 is a flow diagram for a method 220 for determining MTF value(s), color/white balance parameters, and calibration/alignment parameters. In step 222, an image of a target for a set position/orientation is captured by using an imaging device. The imaged target contains features with know target relative coordinates. Step 222 can be accomplished using a calibration fixture, such as one of the above described calibration fixtures. In step 224, the captured image (i.e., image data and/or signal) is processed so as to determine image coordinates for the target features. The image coordinates are associated with the known target relative coordinates by associating target features with image features. The association of target features with image features can be accomplished in a variety of ways, such as by using one of the above described target patterns, preferably a self-referential target pattern. The target relative coordinates and associated image coordinates for the particular captured image can be combined with any possible additional target images at additional positions/orientations for use in determining calibration/alignment parameters.

In step 226, the captured image can be processed to determine one or more MTF values. MTF provides a measure of the imaging system's resolution and can be used for diagnostic purposes. By comparing a measured MTF value with a standard MTF value (i.e., an acceptable MTF value for the imaging system in question), a measure of the functionality of the imaging system can be obtained. Where insufficient resolution functionality is indicated, a status and/or failure message can be generated to communicate that the imaging system has degraded resolution.

An MTF value can be determined by a variety of ways known in the art. The ISO 12233 spatial frequency response evaluation method is one such approach, and is based on an edge-gradient method. (For further discussion, see e.g., Peter D. Burns, "Slanted-Edge MTF for Digital Camera and Scanner Analysis," In *Proc. IS&T* 2000 *PICS Conference*, pg. 135-138, 2000.) An edge-gradient method involves the imaging of an edge feature and processing the image of the edge feature. A key step processing the image of the edge feature is the determination of the location and direction of the edge feature because this has a direct effect on the computed spatial frequency response (SFR). Advantageously, the known location and orientation of the slanted-edge MTF feature 212 in the above described target patterns of FIGS. 9A and 9B relative to the self-referential markers can be used in this determination.

MTF values can be computed for a variety of directions and a variety of positions for each captured image. As such a collection of MTF values can be computed so as to provide sufficient data regarding the health of the imaging system.

In step 228, the captured image can be processed to determine color/white balance parameters. The target patterns of FIGS. 9A and 9B advantageously include a white background, which facilitates the determination of white balance parameters.

Once white balance parameters have been determined, the calibration/alignment parameters can be determined (step 230). In step 230, the resulting collection of associated target coordinates and image coordinate can be used to determine calibration/alignment parameters. In the case of a stereo-imaging device, calibration parameters for the two imaging paths can be use to determine alignment parameters. To determine alignment parameters, a virtual three-dimensional point can be placed in the middle of the camera view volumes with its depth being at a desired distance. The three-dimensional point is then projected into image points by the camera models for the left and right eyes. The difference between the two image points in the image coordinates are the alignment parameters. If necessary (e.g., due to optical assembly inaccuracy, difference in left and right eye optics), the rotation, scale, perspective effect can also be compensated for to make for a better viewing experience from the stereo viewer if the camera parameters are known.

Figure 11:
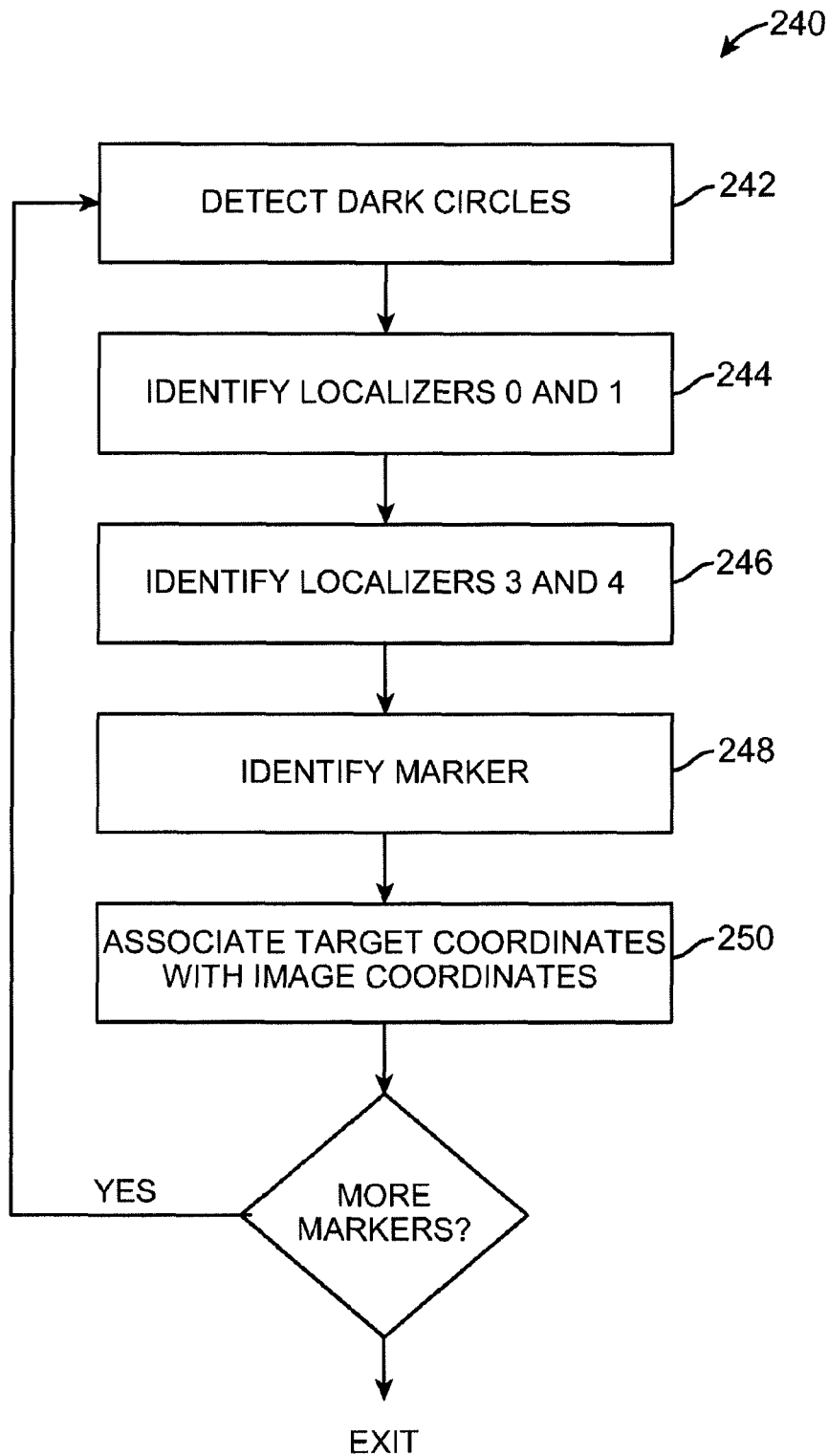
FIG. 11 is a flow diagram for a method for associating target multi-dimensional marker coordinates with associated image coordinates.

FIG. 11 is a flow diagram for a method 240 for processing an image that includes two-dimensional self-referential markers of FIGS. 8, 9A, and 9B so as to associate target coordinates with image coordinates. In general, the processing of images of such markers can use the systems and methods described in commonly owned U.S. patent application Ser. No. 61/204,084, filed Dec. 31, 2008, entitled "Fiducial Marker Design and Detection for Locating Surgical Instrument in Images," which was incorporated by reference above. In step 242, an image is processed to detect dark circle localizer features. In step 244, localizers 0 and 1 are identified by searching for two dark circles (designated in FIG. 8 as "0" and "1") within a minimum and maximum distance and that have a bar (e.g., bar 200) generally between them that is aligned with a line connecting the two circles. By identifying the side of the line that the bar is on, a partial orientation of the pattern can be determined (i.e., about a line in the image). In step 246, localizers 2 and 3 are identified by searching for two dark circles (designated in FIG. 8 as "2" and "3") within a search area relative to the identified localizers 0 and 1. When a calibration fixture is used that constrains the target imaging direction to a predetermined direction for any particular angular position of the target, expected locations for localizers 2 and 3 can be substantially predetermined based on the orientation of the marker as determined by localizers 0 and 1 and their associated bar. In step 248, the marker can be identified by reading the identification dots. Where the identification dots are used for error checking data, the error checking data can be used to validate the identification of the marker. In step 250, the image coordinates for marker features, such as the image coordinates for the dark circle localizer features are associated with their corresponding target relative coordinates.

Method 240 can include some optional steps. For example, Random Sample Consensus (RANSAC) can be used for outlier rejection. By estimating a global alignment transformation for each marker, one can detect the outliers using RANSAC. (For details of RANSAC, see M. A. Fischler and R. C. Bolles, "Random sample Consensus: A paradigm for model fitting with applications to image analysis and automated cartography," Comm. of the ACM, 24: pages 381-395, 1981, which is hereby incorporated by reference.) Additionally, the features of partially visible markers can be used. The features (circles and dots) of partially visible markers are usually in the periphery of an image so that they may contribute more to the estimation of the distortion model than features in the middle of the image. By using a first iteration of calibration parameters, the image locations of the features which are not used in the first iteration are known. A conservative strategy (small distance threshold) can be used to collect such features from the images. All the features can therefore be used for a second calibration iteration.

Figure 12A:
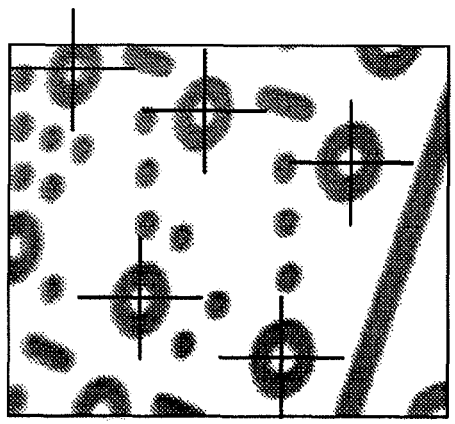
FIGS. 12A through 12E illustrate steps for processing an image so as to identify a calibration target marker.
Figure 12B:
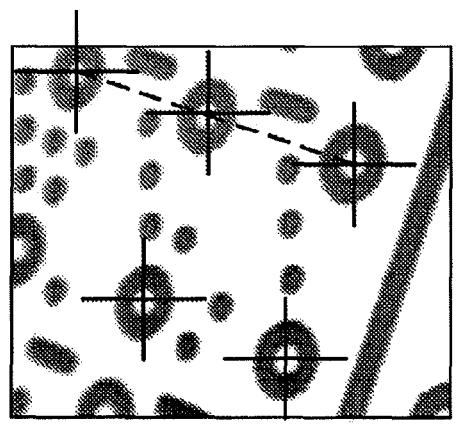
Figure 12C:
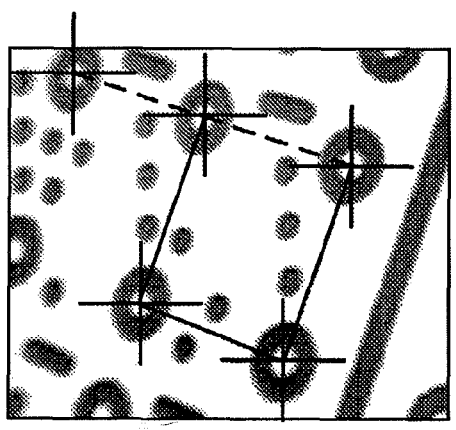
Figure 12D:
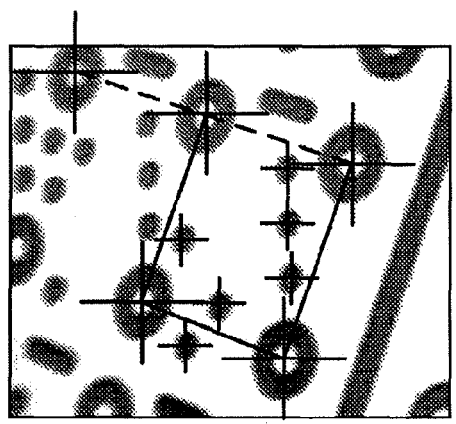
Figure 12E:
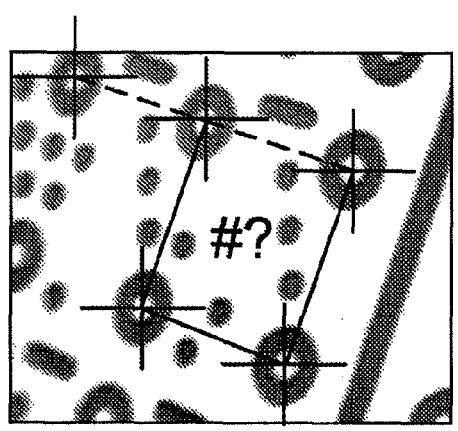

FIGS. 12A, 12B, 12C, 12D, and 12E illustrate the method of FIG. 11 for a single marker. In FIGS. 12A and 12B, the dark circles are detected and localizers 0 and 1 are identified. In FIG. 12C, localizers 2 and 3 are identified. In FIG. 12D a marker identification hypothesis is tested by checking to see whether the image contains identification dots at expected locations. If the marker identification hypothesis is correct, the marker is identified as illustrated in FIG. 12E. The image can also be processed so as to directly detect the presence or absence of identification dots, which can be used to directly determine the identification of the marker.

Figure 13A:
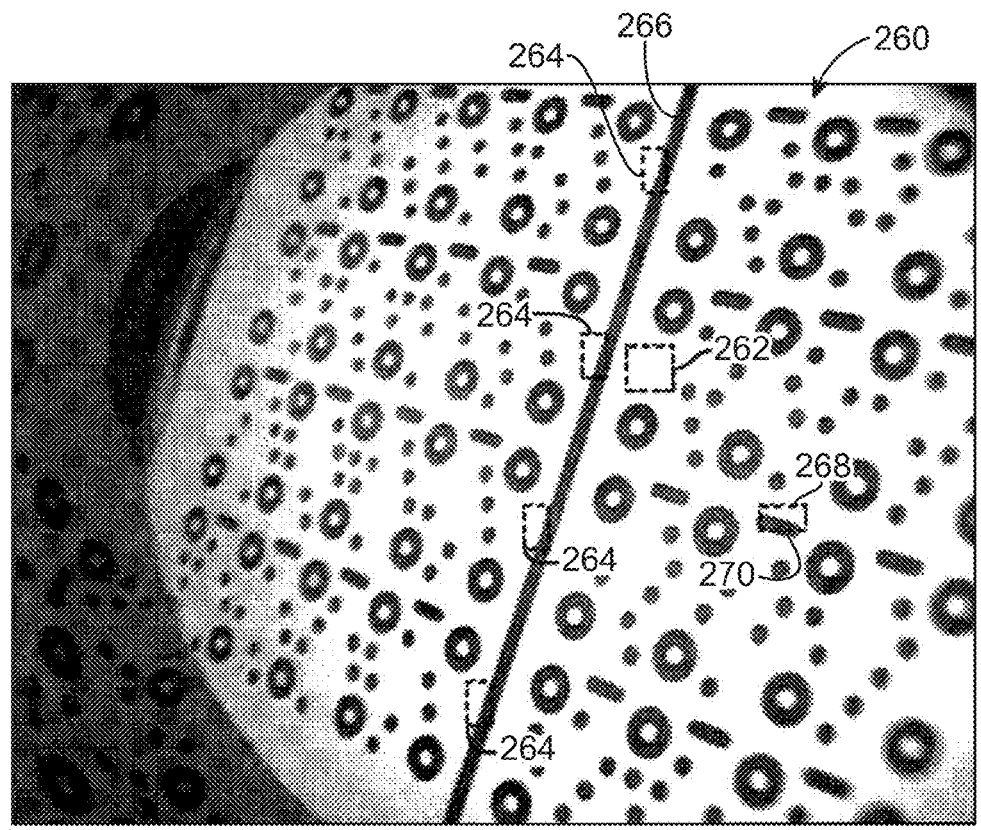
FIG. 13A, illustrates exemplary locations within an image of a calibration target of regions-of-interest that can be processed to determine color/white-balance parameters and modulation transfer function (MTF) values.

FIG. 13A illustrates the location within an image of a calibration target 260 of an exemplary color/white-balance region-of-interest 262 that can be processed to determine color/white-balance parameters. With a determination of the orientation and position of the target within a captured image, a color/white-balance region-of-interest 262 can be selected so as to encompass a sufficient amount of the white background of the target for use in determining color balance parameters, such as white balance parameters. As can be appreciated with reference to FIG. 13A, multiple potential regions-of-interest exist that can be selected for processing to determine color balance parameters. Another approach is to extract the dark patterns and use the resulting image, which contains only white areas, to determine the color balance parameters (e.g., white balance parameters).

Figure 13B:
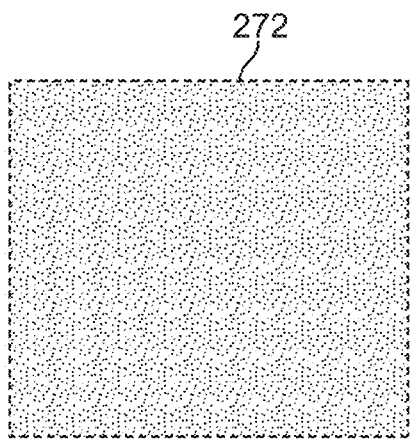
FIGS. 13B and 13C illustrate a non-color balanced region-of-interest of the image of FIG. 13A and a color-balance control.
Figure 13C:
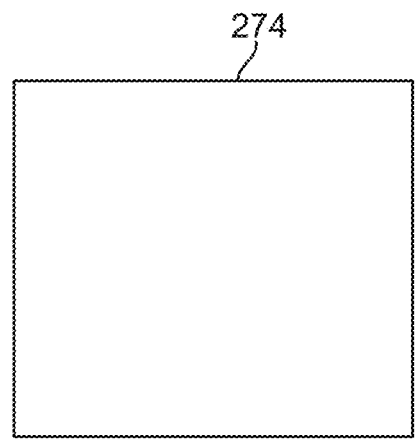

FIG. 13A also illustrates locations of exemplary modulation transfer function (MTF) regions-of-interest that can be processed to determine MTF values. One or more of the slanted-edge MTF regions-of-interest 264 disposed anywhere along slanted-edge feature 266 can be processed to determine MTF values, which can provide diagnostic data for an imaging device at any selected point along the slanted-edge feature 266. A marker bar MTF region-of-interest 268 can also be disposed on a marker bar 270. Accordingly, a combination of MTF regions-of-interest can be selected so as to provide diagnostic data for multiple specific locations throughout an image. Additionally, multiple images can be processed where the slanted-edge feature 266 and marker bars 270 have a different orientation in the image, thereby providing additional image relative locations at which to calculate MTF values. FIGS. 13B and 13C illustrate a color/white balanced region-of-interest 272 of the image of FIG. 13A and a color/white-balance control 274, respectively. Region-of-interest 272, for example, can be any number of regions-of-interest that captures a background region of the target, such as region-of-interest 262 shown in FIG. 13A, which can be selected based upon the target's position and orientation as determined by processing one or more of the marker patterns. The region-of-interest 272 can be processed against the control 274 so as to determine color/white balance parameters. Alternatively, the dark areas can be extracted and the resulting image containing only white areas can be processed against the control 274 so as to determine color/white balance parameters.

Target design variations can be used to provide slanted-edge features at additional orientations that can be used to determine MTF values. Such additional slanted-edge features may reduce the number of images required to generate MTF values for vertical and horizontal image device directions. When determining MTF values for the vertical direction, it can be advantageous to image slanted-edge features that are slanted by a relatively small angle (e.g., by 10 degrees) from the horizontal direction. Likewise, when determining MTF values for the horizontal direction, in can b e advantageous to image slanted-edge features that are slanted by a relatively small angle (e.g., by 10 degrees) from the vertical direction. In one such target design variation, the bar 200 (shown in FIG. 8) can be replaced by a wedge shape having a small angle (e.g., 7 degrees) thereby providing two slanted-edge orientations per bar instead of one. Some, groups, or all of the bars on a target can also be oriented differently, thereby providing additional orientations for any particular camera to target orientation. The shape of the straight dark bar 212 (shown in FIGS. 9A and 9B) can also be modified to provide additional slanted-edge orientations. The straight dark bar can also be augmented with multiple instances disposed at additional orientations (e.g. one vertical and one horizontal).

What is claimed is:

1. A method comprising:
engaging an interface of a body of a calibration target device with a stereoscopic endoscope so as to provide a calibration spatial relationship between the stereoscopic endoscope and a target surface of the calibration target device,
wherein the target surface extends in three dimensions;
wherein the target surface includes a plurality of calibration markers; and
wherein the plurality of calibration markers is distributed within a field of view of the stereoscopic endoscope with a first calibration marker of the plurality of calibration markers extending along a first plane and a second calibration marker of the plurality of calibration markers extending along a second plane, the second plane being different from the first plane and asymetric, relative to the field of view, with the first plane.

2. The method of claim 1, further comprising configuring the interface of the calibration target device for engagement with the stereoscopic endoscope by selectively positioning a first receptacle of the interface in alignment with the target surface, the engaging the interface of the body of the calibration device with the stereoscopic endoscope comprising introducing a distal end of the stereoscopic endoscope into the first receptacle so as to maintain the calibration spatial relationship.

3. The method of claim 2, wherein the interface has a second receptacle alignable with the target surface, the second receptacle being configured to fittingly receive another stereoscopic endoscope having a viewing angle or cross-section different than the stereoscopic endoscope, and wherein the configuring of the calibration target device comprises moving the second receptacle from alignment with the target surface.

4. The method of claim 3, wherein the target surface is supported by a base of the target device, and wherein movement of the interface relative to the base is detent indexed so as to facilitate alignment of the receptacles with the target surface.

5. The method of claim 4, wherein each of the first and second receptacles has an associated indicium identifying a characteristic of endoscopes suitable for calibration with the receptacle, and wherein movement of the interface relative to the base identifies the indicium of the receptacle aligned with the viewing surface.

6. The method of claim 2, wherein a distal end of the stereoscopic endoscope is cylindrical, and wherein the first receptacle tapers radially inwardly from an opening toward an inner end of the receptacle so as to radially engage and position the distal end of the stereoscopic endoscope as the stereoscopic endoscope is inserted into the receptacle.

7. The method of claim 2, wherein a resilient bushing of the first receptacle radially engages the stereoscopic endoscope proximally of the distal end of the stereoscopic endoscope so as to orient the field of view of the stereoscopic endoscope relative to the target surface, and wherein an axial stop of the first receptacle promotes axial alignment of the field of view of the stereoscopic endoscope with the target surface.

8. The method of claim 1, wherein the first plane is offset from the second plane and the first calibration marker is nearer to the stereoscopic endoscope than the second calibration marker.

9. The method of claim 1, wherein the first plane intersects the second plane.

10. The method of claim 9, wherein the plurality of calibration markers includes a third calibration marker, the third calibration marker extending along a third plane of the target surface, the third plane differing from the first and second planes.

11. The method of claim 10, wherein the three planes intersect at a point, wherein a plurality of image markers is disposed along the first, second, and third planes along first, second, and third planar surface regions of the target surface, respectively, and wherein the first, second, and third planar surface regions slope away from the stereoscopic endoscope laterally inwardly relative to the field of view of the stereoscopic endoscope so that an inner portion of the field of view presents far viewing markers while an outer portion of the field of view presents near viewing markers to the stereoscopic endoscope.

12. The method of claim 1, wherein the engaged target device presents an orientation feature of the target surface within an inner portion of the field of view, and wherein the method further comprises manually orienting the target device relative to the stereoscopic endoscope by rotating the target device relative to the stereoscopic endoscope in response to alignment of the orientation feature.

13. The method of claim 12, wherein the target surface is white and the orientation feature comprises an asymmetric aperture, and further comprising axially offsetting the asymmetric aperture along the field of view from any hand or other body supporting the target device with a protrusion of the target device near the aperture.

14. The method of claim 1, the target device being configured to reflect illumination from the stereoscopic endoscope toward the stereoscopic endoscope with a white color of the target surface surrounding the markers so as to facilitate white balancing an image captured by the stereoscopic endoscope.

15. The method of claim 1, wherein the markers differ and each include a plurality of identification features so as allow identification of the differing markers.

16. A calibration target device comprising:
a body having an interface; and
a target surface mounted within the body, the target surface having a plurality of calibration markers including a first calibration marker extending along a first plane and a second calibration marker extending along a second plane, wherein the target surface extends in three dimensions, and wherein the second plane is different from the first plane; and
the interface being configured for engaging a stereoscopic endoscope so as to maintain a calibration spatial relationship between the stereoscopic endoscope and the target surface such that the first and second calibration markers are distributed within a field of view of the stereoscopic endoscope and the second plane is asymmetric, relative to the field of view, with the first plane.

17. The target device of claim 16, wherein the interface comprises a first receptacle configured to be selectively positioned in alignment with the target surface and to maintain the calibration spatial relationship while the stereoscopic endoscope or the body is held manually.

18. The target device of claim 17, wherein the interface is movably coupled to a base of the body and has a second receptacle alignable with the target surface, the second receptacle being configured to fittingly receive another stereoscopic endoscope having a viewing angle or cross-section different than the stereoscopic endoscope so that the target device is reconfigurable by moving the interface to alternate between the second receptacle and the first receptacle being in alignment with the target surface.

19. The target device of claim 18, wherein movement of the interface relative to the base is indexed by detents so as to facilitate alignment of the receptacles with the target surface.

20. The target device of claim 18, wherein each of the first and second receptacles has an associated indicium identifying a characteristic of endoscopes suitable for calibration using the receptacle, and wherein movement of the interface relative to the base identifies the indicium of the receptacle aligned with the viewing surface.

21. The target device of claim 18, the distal end of the stereoscopic endoscope being cylindrical, wherein each of the first and second receptacles tapers radially inwardly from an opening toward an inner end of the receptacle so as to radially engage and axially position a distal end of the stereoscopic endoscope as the stereoscopic endoscope is inserted into the receptacle.

22. The target device of claim 21, wherein a resilient bushing of each of the first and second receptacles is configured to radially engage the stereoscopic endoscope proximally of the distal end of the stereoscopic endoscope so as to axially orient the field of view of the stereoscopic endoscope relative to the target surface, and wherein an axial stop of each of the first and second receptacles is configured to promote axial alignment of the field of view of the stereoscopic endoscope with the target surface.

23. The target device of claim 16, wherein the first plane is offset from the second plane and the first calibration marker is nearer to the stereoscopic endoscope than the second calibration marker when the interface engages the stereoscopic endoscope with the calibration spatial relationship.

24. The target device of claim 16, wherein the first plane intersects the second plane.

25. The target device of claim 24, wherein the plurality of calibration markers includes a third calibration marker, the third calibration marker extending along a third plane, the third plane differing from the first and second planes.

26. The target device of claim 25, wherein the three planes intersect at a point, wherein a plurality of image markers is disposed along the first, second, and third planes along first, second, and third planar surface regions of the target surface, respectively, and wherein the first, second, and third planar surface regions slope away from the stereoscopic endoscope laterally inwardly relative to the field of view of the stereoscopic endoscope so that an inner portion of the field of view presents far viewing markers while an outer portion of the field of view presents near viewing markers to the stereoscopic endoscope.

27. The target device of claim 25, wherein the first, second, and third planes are tangent to the target surface adjacent the first, second, and third calibration markers, respectively, the target surface curving between the first, second, and third calibration markers.

28. The target device of claim 16, further comprising an orientation feature of the target surface disposed within an inner portion of the field of view, wherein the interface is configured to allow rotation of the target device about the stereoscopic endoscope so as to facilitate manually orienting the target device relative to the stereoscopic endoscope by rotating the target device relative to the stereoscopic endoscope in response to alignment of the orientation feature.

29. The target device of claim 28, wherein the target surface is white, wherein the orientation feature comprises an asymmetric aperture, and wherein a protrusion extends axially away from the interface from the aperture so as to offset a hand or other body supporting the target device.

30. The target device of claim 16, wherein the target surface has a white color surrounding the markers so as to facilitate white balancing the stereoscopic endoscope with reflected illumination from the stereoscopic endoscope.

* * * * *